United States Patent
Lee et al.

(10) Patent No.: US 6,300,311 B1
(45) Date of Patent: Oct. 9, 2001

(54) REGULATION OF VERTEBRATE OVARIAN MATURATION AND FUNCTION USING GROWTH FACTORS

(75) Inventors: Vaughan H. Lee; John J. McGlore, both of Lubbock, TX (US)

(73) Assignees: Texas Tech University; Texas Tech Health Sciences Center, both of Lubbock, TX (US)

(*) Notice: Subject to any disclaimer, the term of this patent is extended or adjusted under 35 U.S.C. 154(b) by 0 days.

(21) Appl. No.: 09/212,581

(22) Filed: Dec. 14, 1998

Related U.S. Application Data

(63) Continuation-in-part of application No. 09/060,060, filed on Apr. 14, 1998.

(51) Int. Cl.[7] .......................... A61K 38/18; C07K 14/485
(52) U.S. Cl. .................................. 514/12; 514/2; 530/399
(58) Field of Search ........................... 514/2, 12; 530/399

(56) References Cited

U.S. PATENT DOCUMENTS

| | | |
|---|---|---|
| 4,589,402 | 5/1986 | Hodgen et al. . |
| 4,734,398 | 3/1988 | diZerega . |
| 5,010,055 | 4/1991 | Donahoe . |
| 5,288,705 | 2/1994 | Zohar . |
| 5,395,825 | 3/1995 | Feinberg et al. . |
| 5,496,720 | 3/1996 | Susko-Parrish . |
| 5,523,226 | 6/1996 | Wheeler . |
| 5,563,059 | 10/1996 | Alak et al. . |
| 5,610,138 | 3/1997 | Jacobs . |
| 5,693,479 | 12/1997 | Feinberg et al. . |

FOREIGN PATENT DOCUMENTS

97/38002   10/1997  (WO) .

OTHER PUBLICATIONS

Boland et al. J. Reprod. Fertil. 101:369–374, 1991.*
Westergaard et al. New Trends Gynaecol. Obstet 7(3–4):375–384, 1991.*
Eppig et al. Biol. Reprod. 54:197–207, 1996.*
AR1 "Growth Factors and The Ovary", by Woodruff, et al., *New York Plenum Press*, pp. 291–295 (1989).
AS1 "Epidermal Growth Factor Concentrations and Pig Tissues and Body Fluids Measured Using a Homologous Radioimmunoassay" by Vaughan, et al., *Journ of Endocrinology*, vol. 13, pp. 77–83 (1992).
AT1 See attached pages for additional citations.
"Cellular Hyperplasia in Rats Following Continuous Intravenous Infusion Recombinant Human Epidermal Growth Factor" by Breider, et al., *Vet Pathology*, vol. 33, pp. 184–194 (1996).
"Effect of Milk–Borne Epidermal Growth Factor on the Hepatic Microcirculation and Kupffer Cell Function in Suckling Rats" by McCuskey, et al. *Biology of the Neonate*, vol. 7, pp. 202–206 (1997).

"Epidermal Growth Factor, It's Receptor, and Related Proteins" by Carpenter, et al., *Experimental Cell Research*, vol. 164, pp. 1–10 (1986).
"Rat oocyte maturation in vitro: Relief of cyclic AMP inhibition by gonadotropins" by Dekel, et al. *Proc. Nat'l. Acad.Sci. USA*, vol. 75, No. 9, pp. 4369–4373, (Sep. 1978).
"Metabolism and Effects of Epidermal Growth Factor and Related Growth Factors in Mammals", by Fisher and Lakshmanan, *The Endocrine Review by The Endocrine Society*, vol. 11, No. 3, pp. 418–442 (Aug. 1990).
"Epidermal growth factor and transforming growth factor α", by AW Burgess *British Medical Bulletin*, vol. 45, No. 2, pp. 401–424 (1989).
"Human Epidermal Growth Factor: Isolation and Chemical and Biological Properties (fibroblast growth/competitive binding/urinary polypeptide hormone/corneal epithelium)" by Cohen and Carpenter *Proc.Nat'l Acad. Sci. USA*, vol. 72, No. 4, pp. 1317–1321 (Apr. 1975).
"Epidermal Growth Factor" by G. Carpenter and S. Cohen *Ann. Rev. Biochem.*, vol. 48, pp. 193–216 (1979).
"Response of porcine granulosa cells isolated from primary and secondary follicles to FSH, 8–bromo–cAMO and epidermal growth factor in vitro" by Morbeck, et al., *Journ of Reproduction and Fertility*, vol. 99, pp. 577–584 (1993).
"Development In Vitro of Mouse Oocytes from Primordial Follicles" by Eppig and O'Brien, *Biology of Reproduction*, vol. 54, pp. 197–207 (1996).
"Allosteric Regulation of the Epidermal Growth Factor Receptor Kinase" by Schlessinger, *The Journal of Cell Biology*, vol. 103, No. 6, Pt. 1, pp. 2067–2072 (Dec. 1986).
"The Transforming Growth Factor–β Family" by J. Massagué, *Annu. Rev. Cell Biol.*, vol. 6, pp. 597–641 (1990).
"Transforming Growth Factor–α, A Model for Membrane–Anchored Growth Factors", by J. Massagué, *the Journal of Biological Chemistry*, vol. 265, No. 35, pp. 21393–21396 (Dec. 15, 1990).
"Receptors for Epidermal Growth Factor and Other Polypeptide Mitogens" by G. Carpenter, *Ann. Rev. Biochem.*, vol. 56, pp. 881–914 (1987).

(List continued on next page.)

*Primary Examiner*—Christine J. Saoud
(74) *Attorney, Agent, or Firm*—Dickstein Shapiro Morin & Oshinsky, LLP

(57) ABSTRACT

A method is provided for regulating vertebrate ovarian maturation and function using growth factors by providing an amount of epidermal growth factor to prepubertal ovaries of female vertebrate species including stimulation of primordial follicles and enhancing activation of dormant follicles with the results that the mechanics of the method regulate early development of ovarian follicles. The method provides activation of dormant follicles and early ovarian maturation which is accelerated to the point of producing earlier breeding cycles as well as increasing first litter sizes. The method for regulating vertebrate/mammal ovulation maturation is also directed to increasing the ovulation rate and increasing litter size at an age of normal breeding.

35 Claims, 21 Drawing Sheets

OTHER PUBLICATIONS

"A sensitive enzyme immunoassay system of rat epidermal growth factor in biological fluids and tissue extracts" by T. Joh, et al., *Acta Endocrinologica (Copenh)*, vol. 120, pp. 161–623 (1989).

"Isolation of Rat Epidermal Growth Factor (r–EGF): Chemical, Biological and Immunological Comparisons with Mouse and Human EGF", by Schaudies and Savage, *Comp Biochem. Physiol.*, vol. 84B, No. 4, pp. 497–505 (1986).

"Urogastrone Levels in the Urine of Normal Adult Humans" by Gregory, et al., *Journal of Clinical Endocrinology and Metabolism*, vol. 45, No. 4, pp. 668–672 (1977).

"Antisense Epidermal Growth Factor Oligodeoxynucleotides Inhibit Follicle–Stimulating Hormone–Induced in Vitro DNA and Progesterone Synthesis in Hamster Preantral Follicles" by Shyamai K. Roy and Stanley G. Harris, *Moleucler Endocrinology*, vol. 8, No. 9, pp. 1175–1184 (1994).

"EGF Modulates Phosphoinositide Levels in Ovarian Granulosa Cells Stimulated by Luteinizing Hormone" by C. J. Hubbard, *Journal of Cellular Physiology*, vol. 160, pp. 227–232 (1994).

"The expression of transforming growth factor alpha receptor protein and its activation in chicken ovarian granulosa cells of maturing follicles" by O.M. Onagbesan and M.J. Peddie, *Histochemical Journal*, vol. 30, pp. 647–656 (1998).

"The effect of epidermal growth factor in human granulose cells varies with follicle size" by B.S. Hurst, et al., *J. Endocrinol Invest*, vol. 16, pp. 143–145 (1993).

"Expression of Epidermal Growth Factor and Its Receptor in the Human Ovary during Follicular Growth and Regression" by T. Maruo, et al., *Endocrinology,*, vol. 132, No. 2, pp. 924–931.

"Epidermal Growth Factor Binding Sites in Porcine Granulosa Cells and Their Regulation by Follicle–Stimulating Hormone" by H. Fujinaga, et al., *Biology of Reproduction*, vol. 46, pp. 705–709 (1992).

"Oocyte maturation in humans: the role of gonadotropins and growth factors", by E. Gomez, Ph.D., et al., *Fertility and Sterility*, vol. 60, No. 1, pp. 40–46 (Jul. 1993).

"Transforming Growth Factor–$\beta$ Potentiation of Follicle––Stimulating Hormone–Induced Deoxyribonucleic Acid Synthesis in Hamster Preantral Follicles is Mediated by a Latent Induction of Epidermal Growth Factor" by Shyamal K. Roy, *Biology of Reproduction*, vol. 48, pp. 558–563 (1993).

"Epidermal Growth Factor and Transforming Growth Factor–$\beta$ Modulation of Follicle–Stimulating Hormone–Induced Deoxyribonucleic Acid Synthesis in Hamster Preantral and Early Antral Follicles", by Shyamal K. Roy, *Biology of Reproduction*, vol. 48, pp. 552–557 (1993).

"An Autoregulatory Cascade of EGF Receptor Signaling Patterns the Drosophila Egg" by J. Wasserman and M. Freeman, *Cell*, pp. 355–364 (Oct. 1998).

"Presence of transforming growth factor alpha and epidermal growth factor in human ovarian tissue and follicular fluid" by N. Reeka, et al., *Human Reproduction*, vol. 13, pp. 2199–2205 (1998).

"Epidermal Growth Factor in the Germinal Disc and Its Potential Role in Follicular Development in the Chicken" by K. Volentine, et al., *Biology of Reproduction*, vol. 59, pp. 522–526 (1998).

"Epidermal growth factor combined with recombinant human chorionic gonadotrophin improves meiotic progression in mouse follicle–enclosed oocyte culture" by J. Smitz, et al., *Human Reproduction*, vol. 13, No. 3, pp. 664–669 (1998).

"Immunohistochemical Localization of Epidermal Growth Factor and Its Effect on Granulosa Cell Proliferation in Rat Ovary" by Y. Fukumatsu, et al., *Endocrine Journal*, vol. 42, No. 4, pp. 467–473 (1995).

"Effects of epidermal growth factor on the growth and differentiation of cultured mouse ovarian follicles" by N.I. Boland and R.G. Gosden, *Journal of Reproduction and Fertility*, vol. 101, pp. 369–374 (1994).

"Expression of epidermal growth factors and epidermal growth factor receptor in normal cycling human ovaries" by M. Tamura, et al., *Human Reproduction*, vol. 10, No. 7, pp. 1891–1896 (1995).

"Modulatory Role of Epidermal Growth Factors in Follicle–Stimulating Hormone–Induced DNA Synthesis in Cultured Rat Granulosa Cells" by Liang, et al., *Endocrine Journal*, vol. 41, No. 3, pp. 319–323 (1994).

"Relationship between human oocyte maturity, fertilization and follicular fluid growth factors" by P.G. Artini, et al., *Human Reproduction*, vol. 9, No. 5, pp. 902–906 (1994).

"Follicular development through preantral stages: signaling via growth factors", by S.K. Roy and G.S. Greenwald, *Journal of Reproduction and Fertility*, Supplement 50, pp. 83–94 (1996).

"Epidermal Growth Factor Enhances Oocyte Maturation in Pigs" by J. Ding and G. Foxcroft, *Molecular Reproduction and Development*, vol. 39, pp. 30–40 (1994).

"Role of epidermal growth factor and insulin–like growth factor–I on porcine oocyte maturation and embryonic development in vitro" by C. Grupen, et al., *Reprod. Fertil. Dev.*, vol. 9, pp. 571–575 (1997).

"Cloning and characterization of a gene encoding pig epidermal growth factor" by Pascall, et al., *Journal of Molecular Endocrinology*, vol. 6, pp. 63–70 (1991).

"Mechanism of Action of Epidermal Growth Factor–Induced Porcine Oocyte Maturation" by S. Coskun and Y.C. Lin, *Molecular Reproduction of Development*, vol. 42, pp. 311–317 (1995).

"Epidermal growth factor influences growth and differentiation of rat granulosa cells" by J.J. Bendell and J.H. Dorrington, *Endocrinology*, vol. 127, pp. 533–540 (1990).

"[125I] iodo–epidermal growth factor binding and mitotic responsiveness of porcine granulosa cells are modulated by differentiation and follicle–stimulating hormone", by P.A. Buck and D.W. Schomberg, *Endocrinology*, vol. 1221, pp. 28–33 (1988).

"Modulatory action of epidermal growth factor on differentiated human granulosa lutein cells: Cross–talk between ligand activated receptors for EGF and gonadotropin", by L.T. Budnik and A.K. Mukhopadhyay, *Molecular and Cellular Endocrinology*, vol. 124(1–2), pp. 141–150 (1996).

"Human epidermal growth factor and the proliferation of human fibroblasts" by G. Carpenter and S. Cohen, *Journal of Cellular Physiology*, vol. 88, pp. 227–238.

"Induction of maturation in cumulus cell–enclosed mouse oocytes by follicle–stimulating hormone and epidermal growth factor: Evidence for a Positive stimulus of somatic cell origin" by Downs, et al., *Journal of Experimental Zoology*, vol. 245, pp. 86–96 (1988).

"Transforming growth factor β regulates the inhibitory actions of epidermal growth factor during granulosa cell differentiation" by Feng, et al., *Journal of Biological Chemistry*, vol. 261(30), pp. 14167–14170 (1986).

"Hormonal regulation of rat 17 β–hydroxysteroid dehydrogenase type 1 in cultured rat granulosa cells: Effects of recombinant follicle–stimulating hormone, estrogens, androgens, and epidermal growth factor" by Ghersevich, et al., *Endocrinology*, vol. 135, pp. 1963–1971 (1994).

"Epidermal growth factor and epidermal growth factor receptor in the ovary of the domestic cat (*Felis catus*)" by Goritz, et al., *Journal of Reproduction and Fertility*, vol. 106, pp. 117–124 (1996).

"Stimulation of epidermal growth factor gene expression during the fetal mouse reproductive tract differentiation: Role of androgen and its receptor" by Gupta and Singh, *Endocrinology*, vol. 137(2), pp. 705–711 (1996).

"Modulation of the effects of FSH, androstenedione, epidermal growth factor (EGF) and insulin–like growth factor I (IGF–I) on bovine granulosa cells by GCIF, a growth–inhibitory factor on low molecular mass from bovine follicular fluid" by Hynes, et al., *Journal of Reproduction and Fertility*, vol. 108(2), pp. 193–197 (1996).

"Expression of the genes for the epidermal growth factor receptor and its ligands in porcine corpus lutea" by Kennedy, et al., *Endocrinology*, vol. 132(4), pp. 1857–1859 (1993).

"The inhibitory effects of mullerian–inhibiting substance on epidermal growth factor induced proliferation and progesterone production of human granulosa–luteal cells" by Kim, et al., *Journal of Clinical Endocrinology and Metabolism*, vol. 75(3), pp. 911–917 (1992).

"Follicular development in the neonatal mouse ovary: Effect of epidermal growth factor" by Lintern–Moore, et al., *Acta Endocrinologica*, vol. 96(1), pp. 123–126 (1981).

"Stimulatory effect of insulin–like factor I and epidermal growth factor on the maturation or rabbit oocytes in vitro" by Lorenzo, et al., *Journal of Reproduction and Fertility* vol. 107, pp. 109–117 (1995).

"[125I] iodo–follicle–stimulating hormone binding by cultured porcine granulosa cells" by May, et al., *Endocrinology*, vol. 120(6), 2413–2420 (1987).

"Differential effects of epidermal growth factor somatomedin–c/insulin–like growth factor I, and transforming growth factor–β on porcine granulosa cell deoxyribonucleic acid synthesis and cell proliferation" by May, et al. *Endocrinology*, vol. 123(1), pp. 168–179 (1988).

"Epidermal growth factor acts directly on the sheep ovary in vivo t0 inhibit oestradiol–17β and inhibit secretion and enhance progesterone secretion" by Murray, et al., *Journal of Endocrinology*, vol. 137, pp. 253–264 (1993).

"Epidermal growth factor replaces estrogen in the stimulation of female genital–tract growth and differentiation" by Nelson, et al., *Proceedings of the Nat'l Acad of Sciences of the USA*, vol. 88, pp. 21–25 (1991).

"Epidermal growth factor and c–jun act via a common DNA Regulatory element to stimulate transcription of the ovine p–450 cholesterol side chain cleavage (CYP11A1) promoter" by Pestell, et al., *The Journal of Biological Chemistry*, vol. 270(31), pp. 18301–18308 (1995).

"Mouse prepro–epidermal growth factor synthesis by the kidney and other tissues" by Rall, et al., *Nature*, vol. 313, pp. 228–231 (1985).

"Immunohistochemical localization of epidermal growth factor–like activity in the hamster ovary with a polyclonal antibody" by Roy, et al., *Endocrinology*, vol. 126, No. 3, pp. 1309–1317 (1990).

"Immunoreactivity of antibodies to epidermal growth factor, transforming growth factors, alpha and beta, and epidermal growth factor receptor in the premenopausal ovary" by Scurry, et al., *Pathology*, vol. 26, pp. 130–133 (1994).

"The cytosolic 47–kilodalton protein that binds to the 3' untranslated region of epidermal growth factor transcripts responds to orchiectomy in a tissue–specific fashion" by Sheflin, et al., *Endocrinology*, vol. 137, No. 12, pp. 5616–5623 (1996).

"Gene expression and peptide localization for epidermal growth factor receptor and its ligands in porcine luteal cells" by Singh, et al., *Molecular and Cellular Endocrinology*, vol. 113, vol. 2, pp. 137–143 (1995).

"Epidermal growth factor and its receptor gene expression and peptide localization in porcine ovarian follicles" by Singh, et al., *Molecular Reproduction and Development*, vol. 40, pp. 391–399 (1995).

"Expression of epidermal growth factor receptor in normal ovary and in ovarian tumors" by Stewart, et al., *Int'l Journal of Gynecological Pathology*, vol. 11, pp. 266–272 (1992).

"Epidermal growth factor and basic fibroblast growth factor suppress the spontaneous onset of apoptosis in cultured rat ovarian granulosa cells and follicles by a tyrosine kinase–dependent mechanism" by Tilly, et al., *Molecular Endocrinology*, vol. 6, No. 11, pp. 1942–1950 (1992).

"Expression of epidermal growth factor and its mRNA in pig kidney, pancreas and other tissue" by Vaughan, et al., *Biochemical Journal*, vol. 279, pp. 315–318 (1991).

"Systemic treatment with epidermal growth factor in the rat. Biomechanical properties of the growing small intestine" by Vinter–Jensen, et al., *Regulatory Peptide*, vol. 61, No. 2, pp. 135–142 (1996).

"Chronic administration of epidermal growth factor to pigs induces growth, especially of the urinary tract with accumulation of epithelial glycoconjugates" by Vinter–Jensen, et al., *Laboratory Investigation*, vol. 73, No. 6, pp. 788–793 (1995).

"Presence of transforming growth factor alpha messenger ribonucleic acid (mRNA) and absence of epidermal growth factor mRNA in rat ovarian granulosa cells, and the effects of these factors on steroidogenesis in vitro" by Yeh, et al. *Biology of Reproduction*, vol. 48, pp. 1071–1081 (1993).

\* cited by examiner

FOLLICULAR DEVELOPMENT

DORMANT FOLLICLE 0.05 mm → MATURE FOLLICLE 8–11 mm → OVULATED EGG

FIG. 2
REGULATION OF FOLLICULAR DEVELOPMENT
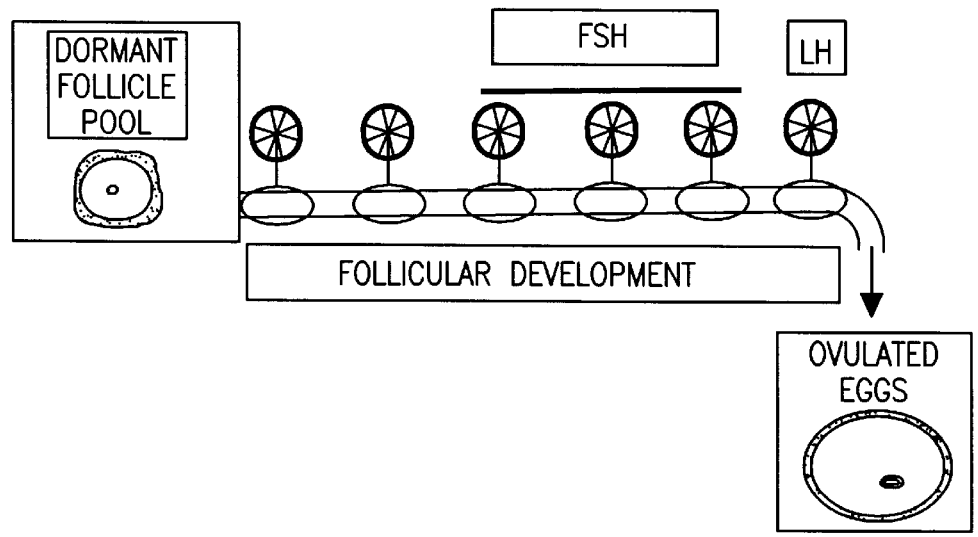
FIG. 3  HOW TO STUDY INITIAL STEPS OF FOLLICULAR DEVELOPMENT
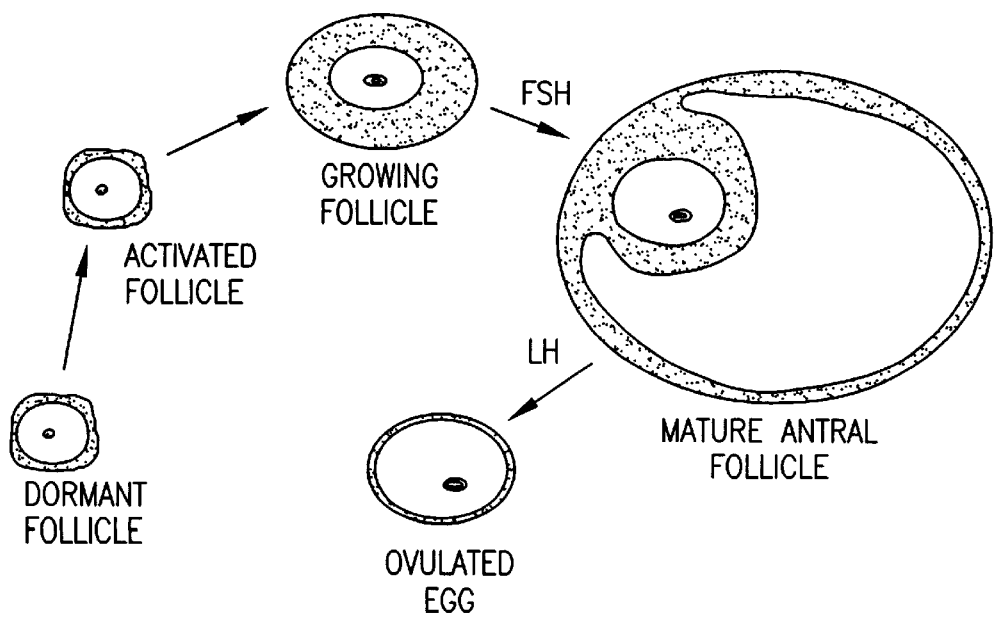

STAGES OF FOLLICULAR DEVELOPMENT IN PREPUBERTAL RABBITS

PRIMORDIAL FOLLICLE
14 d.pp.

PRIMARY FOLLICLE
28 d.pp.

SECONDARY FOLLICLE
42 d.pp.

TERTIARY FOLLICLE
56 d.pp.

FOLLICLE POPULATION IN DEVELOPING RABBIT OVARIES

EFFECT OF GROWTH FACTORS ON R55 EXPRESSION
IN IMMATURE RABBIT OVARIES

FIG. 11
OVARIAN MATURATION
IMMATURE 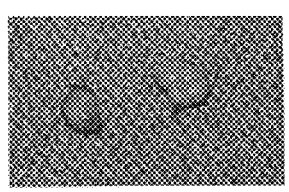 MATURE 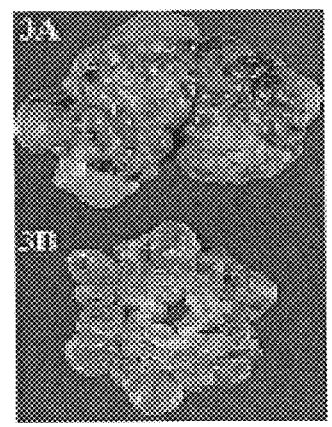

FOLLICLE POPULATION IN IMMATURE PIG OVARIES
DAY 70 POSTPARTUM

FOLLICULAR DEVELOPMENT DURING
OVARIAN MATURATION

FIG. 18

DNA AND AMINO ACID SEQUENCE OF THE RECOMBINANT PIG EGF

JULY 23, 1998  13:20

```
      ATGAGAGGATCGCATCACCATCACCATCACGGATCCAATAGTTACTCTGAATGCCCGCCG
   1 ------+------+------+------+------+------+ 60
      TACTCTCCTAGCGTAGTGGTAGTGGTAGTGCCTAGGTTATCAATGAGACTTACGGGCGGC a      M   R   G   S   H   H   H   H   H   H   G   S   N   S   Y   S   E   C   P   P   -

TCCCACGACGGGTACTGCCTCCACCGTGGTGTGTGTATGTATATTGAAGCCGTCGACAGC
  61 ------+------+------+------+------+------+ 120
      AGGGTGCTGCCCATGACGGAGGTGCCACCACACACATACATATAACTTCGGCAGCTGTCG a      S   H   D   G   Y   C   L   H   G   G   V   C   M   Y   I   E   A   V   D   S   -

TATGCCTGCAACTGTGTTTTTGGCTACGTTGGCGAGCGATGTCAGCACAGAGACTTGAAA
 121 ------+------+------+------+------+------+ 180
      ATACGGACGTTGACACAAAAACCGATGCAACCGCTCGCTACAGTCGTGTCTCTGAACTTT a      Y   A   C   N   C   V   F   G   Y   V   G   E   R   C   Q   H   R   D   L   K   -

TGGTGGGAGCTGCGCAAGCCGAATTCGAGCTCGTACCCGGGGTCCTCTAGAGTTGACCTG
 181 ------+------+------+------+------+------+ 240
      ACCACCCTCGACGCGTTCGGCTTAAGCTCGAGCATGGGCCCCAGGAGATCTCAACTGGAC a      W   W   E   L   R   K   P   N   S   S   S   Y   P   G   S   S   R   V   D   L   -

CAGCCAAGCCGATAG
 241 ------+----  255
      GTCGGTTCGGCTATC a      Q   P   S   R   *   -
```

FIGURE 18. THIS IS THE DNA AND AMINO ACID SEQUENCES OF THE rec-pEGF PROTEIN BEING EXPRESSED IN THE BACTERIAL SYSTEM. IT CONTAINS THE 6X HISTADINE TAG AT THE NH4 TERMINAL, THE 53 AMINO ACIDS OF PIG EGF (100 % IDENTICAL TO PUBLISHED SEQUENCE FOR PIG), AND 19 AMINO ACIDS FROM THE BACTERIAL PLASMID VECTOR.

FIG. 19

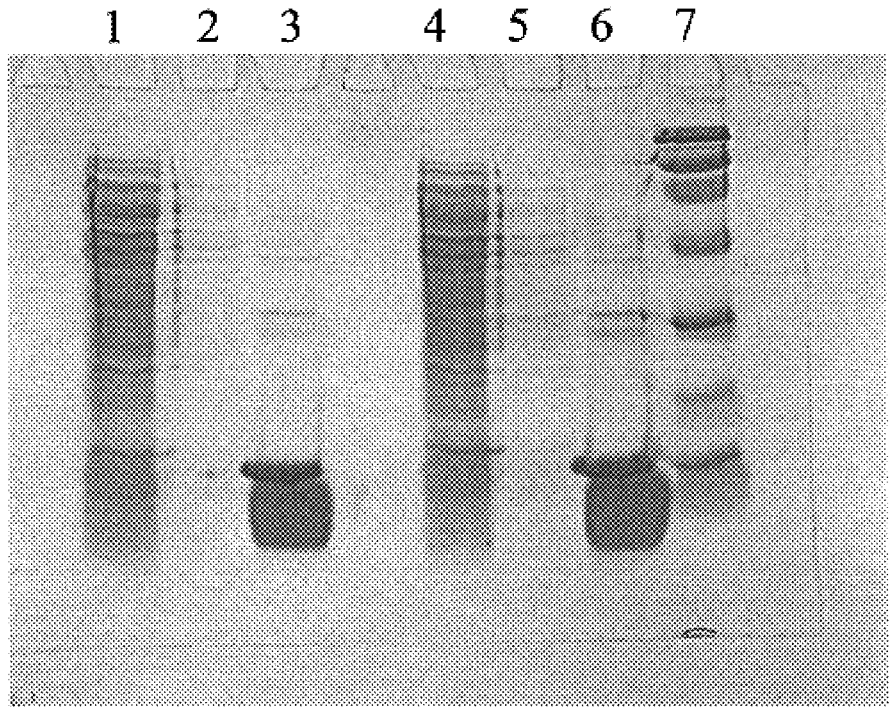

LANE 1: LP6A-SP1 FLOW THROUGH (UNBOUND BACTERIAL PROTEINS).
LANE 2: LP6A-SP1 BUFFER WASH OF COLUMN.
LANE 3: LP6A-SP1 ELUTED rec-pEGF FROM COLUMN.
LANE 4: LP6B-SP1 FLOW THROUGH (UNBOUND BACTERIAL PROTEINS).
LANE 5: LP6B-SP1 BUFFER WASH OF COLUMN.
LANE 6: LP6B-SP1 ELUTED rec-pEGF FROM COLUMN.
LANE 7: RAINBOW MOLECULAR WEIGHT MARKERS.

FIGURE 19. THE EXPRESSED rec-pEGF PROTEIN WAS PURIFIED ON Ni-AGAROSE COLUMNS AND ANALYZED ON 15% POLYACRYLAMIDE SDS GELS. THIS PICTURE IS A REPRESENTATIVE SAMPLE OF SOME OF THESE GELS SHOWING TWO PURIFIED SAMPLES OF rec-pEGF. LANES 3 AND 6 DEMONSTRATE A RELATIVELY PURE SAMPLE OF rec-pEGF AT A RELATIVE MOLECULAR WEIGHT OF ~10 KILODALTONS (PREDICTED MOLECULAR WEIGHT FROM AMINO ACID SEQUENCE).

FIGURE 21. BIOASSAY FOR RECOMBINANT PIG EGF (rec-pEGF). NOTE THAT INCREASING CONCENTRATIONS OF pEGF CAUSE AN INCREASE IN UPTAKE OF TRITIATED TYMIDINE.

FIGURE 22. GRAPH OF THE AVERAGE SIZE OF THE TEN LARGEST FOLLICLES OBSERVED IN H/E STAINED SECTIONS OF OVARIES FROM PIGS IN THE PILOT STUDIES. DIAMETERS OF FOLLICLES WERE MEASURED WITH AN OCULARMICROMETER AND ONLY SECTIONS THROUGH THE CENTER OF A FOLLICLE (GERMINAL VESICLE PRESENT) WERE USED FOR THESE EVALUATIONS.

FIG. 23

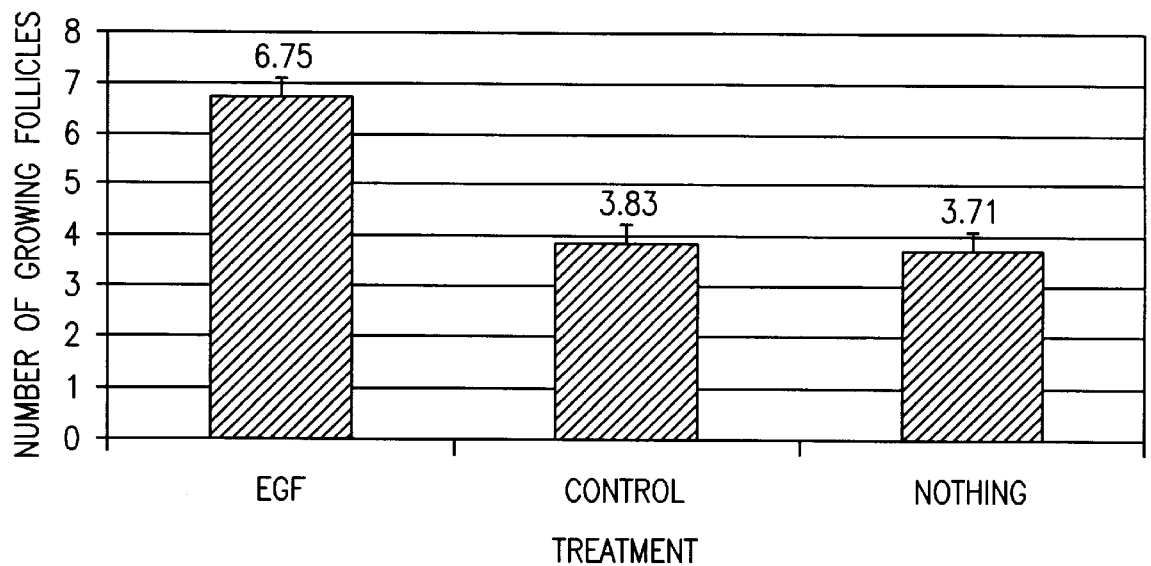

FIGURE 23. NUMBERS OF FOLLICLES WERE INCREASED BY APPLICATION OF EGF. OVARIES WERE EXAMINED AT 70 DAYS OF AGE WHEN THE FIRST COHORT OF GROWING FOLLICLES ARE EXPECTED TO BE PRESENT. GRAPH OF THE AVERAGE NUMBER OF GROWING FOLLICLES IN A DEFINED AREA OBSERVED IN H/E STAINED SECTIONS OF OVARIES FROM PIGS IN THE PILOT STUDIES. NUMBER OF GROWING FOLLICLES WERE COUNTED IN A FRAME (960 X 1400 μm) AND ONLY SECTIONS THROUGH THE CENTER OF A FOLLICLE (GERMINAL VESICLE PRESENT) WERE USED FOR THESE EVALUATIONS. GROWING FOLLICLES WERE IDENTIFIED BASED ON THE PRESENCE OF AT LEAST ONE CUBOIDAL LAYER OF GRANULOSA CELLS SURROUNDING THE OOCYTE.

REGULATION OF VERTEBRATE OVARIAN MATURATION AND FUNCTION USING GROWTH FACTORS

CROSS-REFERENCE TO RELATED APPLICATIONS

This application is a continuation-in-part of a co-pending patent application filed with the United States Patent and Trademark Office on Apr. 14, 1998, by Vaughan H. Lee and John J. McGlone, entitled REGULATION OF VERTEBRATE OVARIAN MATURATION AND FUNCTION USING GROWTH FACTORS, Ser. No. 09/060,060.

FIELD OF THE INVENTION

The invention relates to a method for accelerating maturation of the ovary in mammalian and vertebrate subjects through use of growth factors as a promoter of follicular development and ovulation. In another aspect, the invention relates to the treatment of prepubertal mammals and vertebrate subjects with Epidermal Growth Factor (EGF) to regulate and accelerate ovarian maturation and function.

BACKGROUND OF THE INVENTION

In the arena of mammalian reproduction, many diagnostic and therapeutic procedures exist to aid the reproduction practitioner in making a diagnosis and choosing an appropriate course of action. In mammalian embryology, the mammalian oocyte enters the first meiotic division during fetal life, but becomes arrested in late prophase (in the dictate or diffuse diploid stage of meiosis) before or just after birth (Beaumont, H. M., et al., *Proc. R. Soc. London* (Series Biological Sciences) 155:557–579 (1962). Resumption of meiosis normally does not occur until shortly before ovulation when previously unidentified growth factor trigger ovarian development, followed by a surge of gonadotropins prompts the resumption of meiotic maturation (Dekel, N., et al., *Proc. Nat'l Acad. Sci. U.S.A.*, 75:4369–4373 (1978).

Currently infertility in humans ranges from approximately 10–15% of couples and the risk of infertility is doubled for women between the ages of 35–44 as compared to women between the ages of 30–34. In the United States, the majority of infertility can be accounted for by problems in the female. is a basement membrane protein that must be synthesized and secreted as the follicle grows. It is another marker specific for granulosa cell differentiation and development in early stages of follicular growth. Another study that was published by Vinter-Jensen et al., 1995 looked at the treatment of mini-pigs with EGF. In these studies it was found to stimulate growth of heart, liver, and urinary tract. However, reproductive organs were not closely evaluated in these studies. Other indirect support has been shown in different species. Eppig and O'Brien published in 1996 that treatment with EGF of neonatal mouse ovaries collected and cultured in vitro, increased the number of eggs recovered for in vitro maturation and fertilization. Again this is consistent with our hypothesis that EGF enhances follicular development. Another study published in 1996 by Breider, et al., the investigator looked at the effect of EGF on mature rats. In this study EGF was intravenously infused for a four-week period into mature rats and multiple organs and tissues were evaluated. Overall, EGF stimulates growth and proliferation of many tissues. Specifically in the ovaries of these animals, the ovarian weights were increased which was accompanied by the increase in the number of corpora lutea (CL) found in these ovaries. The CL is a structure that results from the ovulation of a mature antral follicle. This means that in the ovaries there were increased numbers of ovulations. Again, these studies were done in live animals demonstrating the feasibility of using in vivo treatments with EGF.

Epidermal Growth Factor is a peptide hormone that stimulates the growth and differentiating of epidermal tissues during embryogenesis (Carpenter, G., et al., *Exper. Cell. Res.* 164-1-10 (1986); Kris R. M. et al., *Bio-Technol.* 3:135–140 (1985)). EGF may be purified from natural sources or may be obtained through application of recombinant DNA technology.

EGF is a 53-residue polypeptide (M, –6000) that is mitogenic for a variety of cell types both in vivo and in vitro (Carpenter & Cohen, 1979). EGF was originally purified from the male mouse submaxillary gland (SMG) (Cohen 1962) and subsequently from human urine (Cohen & Carpenter, 1975; Gregory, 1975). Antibodies raised against mouse or human EGF are used to confirm expression in tissues or body fluids using immunoassays or immunocytochemical staining. Highest levels of EGF have been found in SMG (mouse), kidney, pancreas, duodenum, urine and milk (see Carpenter, 1985; Gregory, 1985; Burgess, 1989; Fisher & Lakshmanan, 1990). However, there is little information regarding EGF expression in other species because antisera against EGF show very little cross-species reactivity (Gregory, Holmes & Willshire, 1979; Schaudies & Savage. 1986) necessitating the development of homologous immunoassays (Joh. Itoh, Yasue et al. 1989). Despite their limited immunological cross-reactivity, both mouse and human EGF bind to cellular receptors on various cell types from several species with very similar affinities and efficacy (see Carpenter & Cohen, 1979; Carpenter, 1987). While heterologous radioreceptor assays are therefore possible, they lack specificity since other polypeptides (e.g. transforming growth factor alpha (TGF-alpha) are known to bind to the same receptors (see Burgess, 1989; Massague, 1990). In addition, indirect modulation of EGF receptor affinity by heterologous ligands has been widely reported (see Schlessinger. 1986).

A homologous radioimmunoassay for the measurement of EGF levels in pig tissues and body fluids has been developed using an antiserum to recombinant porcine EGF. The assay is highly specific, showing no cross-reactivity with a variety of other polypeptides including the structurally related protein, transforming growth factor-alpha. Furthermore, <1% cross-reactivity was observed with mouse EGF emphasizing the necessity for homologous assays for EGF measurement. Immunoreactive EGF was present in extracts of pig kidney and pancreas (3.44+1–0.43 and 0.76±0.13 (S.E.M.) pmol/g wet weight respectively), but was not detected in extracts of submaxillary gland or liver. Although immunoreactive EGF was not detectable in uterine, allantoic or ovarian follicular fluids, colostrum contained EGF at biologically active concentrations. Immunoreactive EGF was also present in pig urine, with similar concentrations in samples from male or female animals. In addition, pig urine inhibited the binding of I-labeled EGF to 3T3 fibroblasts and stimulated DNA synthesis in quiescent monolayers of these cells, indicating that the immunoreactive material in urine is biologically active. Quantitative comparisons of the data presented here with that published previously indicate considerable species variation in the EGF levels of various tissues and body fluids.

In follicular development, the development of a dormant primordial follicle into a large mature follicle must occur before the ultimate mature follicle is stimulated to ovulate and produce fertilized eggs. This general process is the key for the production of eggs in many species. The ovary is basically a reservoir of dormant follicles and through the process of follicular development, some of these dormant follicles will develop and mature to subsequently produce hundreds to thousands of eggs. Follicular development can be envisioned as a pipeline and the control of the process consisting of many valves or potential regulatory steps. In the later stages of follicular development, it is known that Follicle Stimulating Hormone (FSH) is important for growth and development of mature antral follicles and ultimately Luteinizing Hormone (LH) stimulates the ovulation of a mature follicle and the production of the egg. However, the factors regulating early steps of follicular development have been unknown.

The present invention provides understanding and procedural methods of how some of these early regulatory points are controlled in ovarian follicle development and have applications to mammals and vertebrate animals. For example, methods of the present invention applies to bovine, equine, porcine, canine, feline, human mammals, birds, fish, reptiles and the like. Applications of this technology will benefit farm animals, humans, endangered species, zoo animals and farmed birds and fish.

SUMMARY OF THE INVENTION

The present invention is directed to a method of initiating and regulating ovarian follicular development in mammalian females. Markers have been identified which are initially transcribed in activated primordial follicles in rabbits and pigs. Expression of two rabbit zona pellucida genes R55 and R75, were localized in prepubertal rabbit ovaries by in situ hybridization. Results indicate that transcription of the genes occur initially in activated follicles and increases through early stages of follicular development. Expression of the R55 and/or R75 genes offers a qualitative method to identify activated follicles in vivo and a quantitative method to activate follicular development in vitro.

In addition to permitting identification of morphological changes and granulosa cell proliferation, these gene markers provide functional definitions for the initial steps in folliculogenesis. To determine whether growth factors can stimulate activation of primordial follicles, tissue explants from immature rabbit ovaries (14 days old) were cultured with or without mouse EGF. Ovaries at this age contain only primordial follicles providing an ideal population in which to study activation of follicular development. The relative amounts of R55 mRNA were measured by Northern blot analysis. The Northern blot assay results indicated that EGF (50 ng/ml) increased expression of R55 in primordial rabbit ovarian follicles. It was concluded that EGF stimulates expression of zona pellucida genes in primordial follicles and enhances the level of activation of dormant follicles. The ability to regulate timing and magnitude of follicle activation can influence the overall reproductive capacity of a given female and lead to new methods for managing reproductive function in clinical or agricultural settings.

In another aspect, the invention is directed to another mammal, swine. Swine production is limited, in part, because during early breading cycles relatively few ova are ovulated, resulting in small litter sizes in young sows. Thousands of ovarian follicles containing eggs are formed in new born animals and are available to be activated, but for unknown reasons only a few mature in early estrus cycles. By accelerating earlier activation of dormant ovarian follicles and earlier ova maturation, the present invention provides a method for enhancing productive efficiency in sows accelerating breeding cycles and increasing earlier litter sizes.

Rabbits have ovarian development patterns similar to pigs. The rabbit model was employed to model swine ovarian development. Rabbit test results indicate that activation of dormant follicles and expression of the rabbit R55 zona pellucida gene are increased approximately three fold by treatment of prepubertal ovaries with EGF. Pig follicles synthesize a zona pellucida molecule, ZP3α, which is 74% identical to rabbit R55 and is detectable with molecular probes to R55. This molecular marker for activation and techniques established in the rabbit model was used for studies with pig ovaries.

Confirming these findings in two distinct mammalian species, namely rabbit and swine, suggests a commonality to all vertebrates and mammals that the mechanism of early follicular activation may be accelerated by administering EGF.

BRIEF DESCRIPTION OF THE FIGURES

FIG. 2 is a schematic diagram presenting the many potential steps and control points for follicular development;

FIG. 3 is a diagram showing the later stages of follicular development which occur at growing follicles when they respond to stimulation by FSH and where they mature into antral follicles;

FIG. 11 is a representation to ovarian development in prepubertal pigs;

FIG. 18 is the DNA and amino acid sequences of the recombinant porcine EGF (rec-pEGF) protein, which is expressed, in the bacterial system.

FIG. 19 is a representative sample of 15% polyacrylamide SDS gels of expressed rec-pEGF protein purified in Ni-Agarose columns.

FIG. 23 is a graph illustrating the number of growing ovarian follicles at 70 days of age for the EGF administered group, a control group and a group administered nothing.

DETAILED DESCRIPTION OF THE INVENTION

Figure 1:
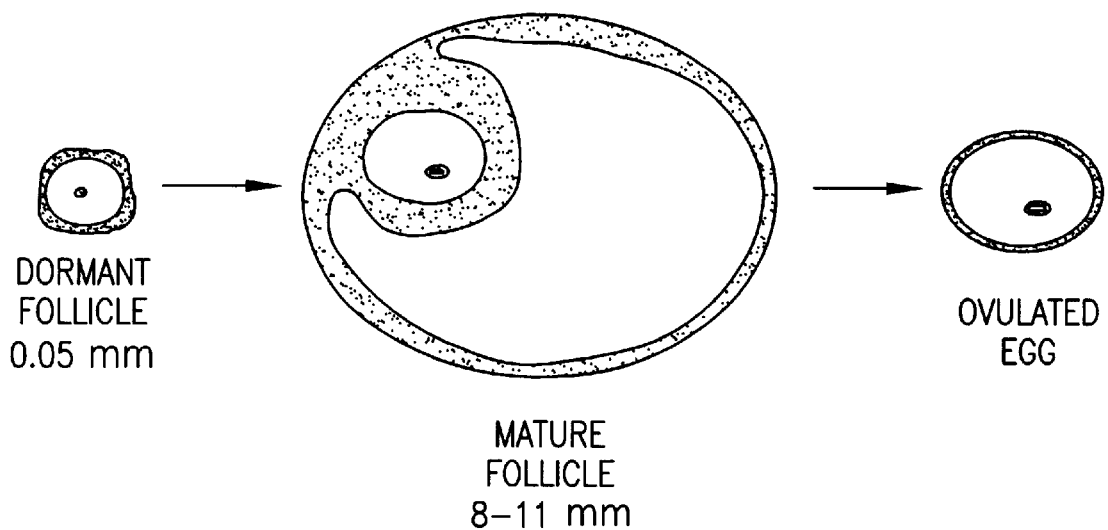
FIG. 1 is a diagram showing a generalized overview of follicular development.

Sows are polyestrous with a period of lactational anestrus occurring until after weaning. The estrus cycle length averages 21 days. Return to estrus occurs after the recovery period, or 4–7 days post-weaning. Estrus onset is marked by the preovulatory surge of LH. Gilts come in to first estrus around 8 months of age. Estrus (heat behavior) occurs for 2–3 days, averaging 60 hours in mature sows, but is only about 48 hours long in gilts. Ovulation actually occurs during the last third of estrus.

Ovulation occurs 36 to 42 hours after the onset of standing heat in mature sows, about 12 hours earlier in gilts. On average, 10–20 ova are shed from follicles ranging from 0.7 to 1.0 cm. Fecundity is highest in sows at 2 to 4 years of age. Gilts average 10–15 ova per cycle. Embryonic survival rate is 65%–75%, resulting in litter sizes of 8 to 12 piglets. Heritability of litter size is low, but tremendous breed differences exist. Recent studies suggest fecundity may be linked to the presence of a specific estrogen receptor. In addition, fecundity is strongly linked to lactational feed intake. Limiting feed intake in gestation leads to greater feed intake during lactation. High feed intake in lactation results in good milk production, high piglet weights at weaning, short wean to estrus intervals, and maximal ovulation rates.

The zona pellucida (ZP) matrix surrounding oocytes appears in follicles following activation, indicating transcription of ZP genes is specifically development. The protein and mRNAs for the rabbit 55 kD ZP component, R55, are initially expressed in oocytes of activated follicles prior to morphological changes. Preliminary results indicated that pig ZP proteins are expressed in activated follicles and show that expression of the pig homologue to R55, ZP3α, provides a marker for determining initiation of follicular development in this species. An objective of the present invention is to determine that EGF stimulates activation of pig primordial follicles, subsequently resulting in expression of ZP genes by oocytes and accelerates the early stages of follicular development. Thus, ZP markers can provide an objective method for measuring follicle activation and development in addition to more subjective observations based on morphological changes. Furthermore these experiments are necessary to determine effectiveness for using EGF to accelerate prepubertal ovarian development in neonatal pigs and ultimately increase reproductive efficiency. An increase of even 10% of pigs per litter would be economically significant for commercial pork producers.

Before development begins follicles are called primordial or dormant follicles and consist of undifferentiated squamous granulosa cells surrounding an oocyte arrested in prophase I of meiosis. When follicles are activated, granulosa cells proliferate and differentiate, while oocytes enter a growth phase. During these early steps of follicular development ZP proteins (rabbit R55 and pig ZP3α) are synthesized and assembled around the oocyte. Recent studies have begun to utilize culture systems to study regulation of these early stages of folliculogenesis. In preliminary observations R55 sense (+) and antisense (−) RNA probes were labeled with $[35^5]$-UTP and used for in situ hybridization to determine the spatio-temporal pattern of expression of R55 during early rabbit ovarian development. Ovaries were collected from prepubertal rabbits (14 and 28 days postpartum, d.pp.), fixed in 4% paraformaldehyde, embedded in paraffin, and sectioned for localization of R55.

Localization of R55 protein and mRNA in activated and growing follicles of prepubertal rabbit ovaries was demonstrated. In 14 d.pp. ovaries, R55 protein and mRNA were localized in oocytes of some primordial follicles but are undetectable in the majority of primordial follicles. It was illustrated that R55 protein and MRNA are abundant in oocytes of primary follicles from 28 d.pp. animals. Expression of R55 was increased in transitional follicles which exhibited characteristics of both primordial and primary follicles. In the cortex of ovaries from 28 d.pp. animals, many of the primordial follicles closest to the medullar region of the ovary are expressing R55 while it is undetectable in the cortical follicles. The position of these labeled primordial follicles indicated that they are the activated group of follicles that will develop during the peripubertal period of folliculogenesis. This spatio-temporal pattern of expression for R55 indicates that transcription of this gene is initiated in oocytes during the activation of follicular development.

Rabbit Ovary Culture

A method to culture pieces of ovaries from 14 d.pp. rabbits was developed, modeled after techniques used for ovaries from neonatal mice and bovine embryos. Tissue pieces (1–2 mm$^3$) from 14 d.pp. rabbit ovaries containing only primordial follicles were placed in cell culture inserts with 3.0 mm pores and cultured in 24-well plates with 300 microliters medium (50–50 blend of (a) F-12 Nutrient Mixture (Ham)(1×), liquid contains L-glutamine, and (b) Medium 199 (1×), liquid contains Earle's modified salts, 1.250 mg/L sodium bicarbonate, and L-glutamine.

Rabbit Ovary Cultures: Treatment with EGF

Cultures were treated with mouse EGF (50 ng/ml) and analyzed for the level of expression of R55 mRNA. Treatment with EGF produced a 3-fold increase in amount of R55 mRNA (normalized to 28 S) as compared to controls incubated in medium alone (FIG. 3). These results suggest that EGF stimulates activation of follicular development and expression of R55 in dormant primordial follicles.

Swine Ovary Cultures: Treatment with EGF

For in vitro experiments, ovaries from prepubertal pigs (3–5 weeks post partum) were collected for tissue cultures of ovarian pieces. The ovaries contained a large population of dormant primordial follicles similar to 14 d.pp. rabbits. Pig ovarian tissue cultures were treated with EGF at different doses for 6 days and tissues collected for in situ hybridization and Northern blot analysis of ZP3α. The 6 day culture period was chosen because in preliminary experiments with cultures of rabbit ovarian tissue, treatment with EGF (50 ng/ml) produced significant increases in expression of R55.

In vivo EGF: Swine

For in vivo experiments, prepubertal pigs at different ages (1, 35, and 70 d.pp.) were treated with subcutaneous osmotic pumps delivering constant daily dosages of EGF for fourteen days. Ovaries were removed following treatments to evaluate follicle development. In ovarian tissue from in vitro and in vivo experiments, expression of ZP3α MRNA was localized by in situ hybridization and the percentage of activated primordial follicles determined. The amount of ZP3α mRNA in cultured pig ovarian tissue was determined by Northern blot analysis to quantitate the level of ZP expression (normalized to levels of 28S RNA).

Two groups of young female pigs were administered recombinant porcine EGF (rec-pEGF). Group 1, aged 30 d.pp., were given 540 μg/day rec-pEGF using subcutaneous osmotic pums, for fourteen days. A control group of the same age were administered the injection vehicle only. A nontreated group was maintained under identical conditions as the control group and Group 1. Group 2, aged 21 d.pp., were given 600 μg/day rec-pEGF for fourteen days.

After fourteen days post-treatment, the Group 1 pigs were necropsied and histological evaluation of ovarian sections (hematoxylin/eosin stained) revealed larger ovarian follicles and the presence of a 70% greater population of growing follicles in the rec-pEGF treated animals than in the control or non-treated groups.

Figure 22:
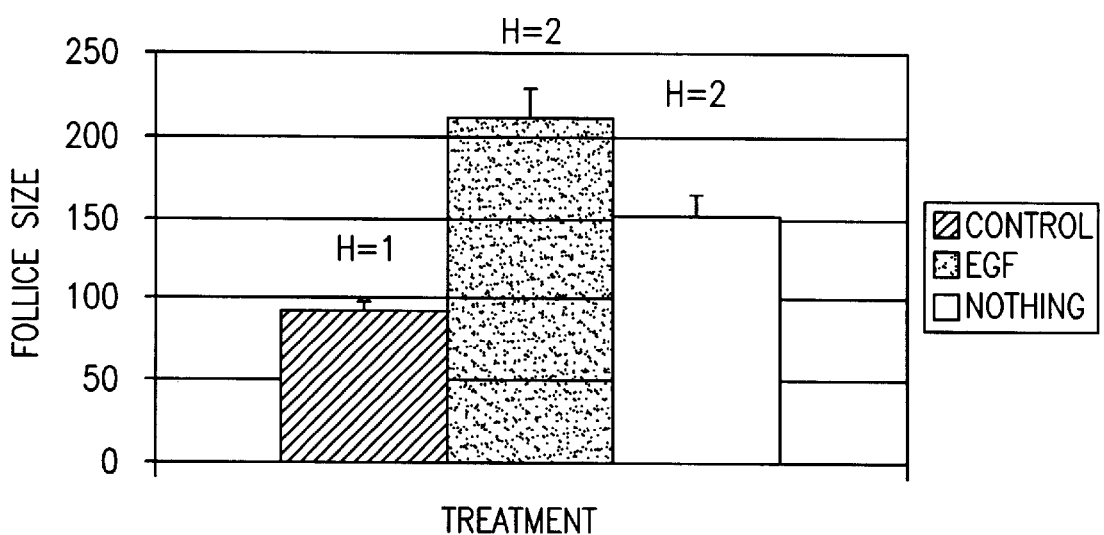
FIG. 22 is a graph depicting the average size of the ten largest follicles observed in H/E-stained sections of pig ovaries, comparing the EGF administered group, with a control group and a group administered neither the EGF or a placebo.

The Group 2 pigs were grown to 10 weeks of age, then necropsied. At the time of necropsy, the pigs receiving rec-pEGF showed no negative effect on weight gain or organ development. The ovaries of the Group 2 pigs showed an almost 100% increase in size when the tissues were collected at 10 weeks of age, when compared to the control group and the group treated with nothing. FIGS. 22 and 23 set forth the foregoing results of the Group 1 and Group 2 pigs.

All pigs in Group 1 and in Group 2 were dosed using subcutaneously placed osmotic pumps. During the time of rec-pEGF, both groups were individually housed, with general health, feeding and behavioral observations made regularly and recorded.

Summary of in vitro and in vivo Results

The foregoing tests demonstrate that EGF stimulates expression of ZP3α and activates primordial follicles in vitro and in whole ovarian cultures. EGF stimulates activation of dormant pig follicles. EGF (50 ng/ml) stimulates DNA synthesis in granulosa cells from primary pig follicles and expression of FSH receptors in granulosa cells from antral pig follicles.

In pigs, an activated primordial follicle matures to antral stage in approximately 84 days and from activation to ovulation will be about 100 days. Therefore, normally follicles that ovulate in the first cycle were activated around day 50 post partum. The process can be accelerated (as we have shown) by application of EGF before day 50 post partum to activate ovarian and follicular development. The inventive goal is to increase the number of primordial follicles activated earlier in prepubertal development, thus increasing the number of growing follicles. Subsequent treatment with gonadotropins will result in more mature follicles at earlier ages in young sows. Further development of this model should result in larger and earlier litters in production sows.

Experiments on pigs demonstrate that pig ZP3α is expressed during activation of dormant primordial follicles and determines the period of prepubertal ovarian development during which follicle activation is greatest. In prepubertal pig ovaries, dormant primordial follicles are located in the outer portion of the cortex while activated and growing follicles are found close to the medullar region. Since ZP3α is expressed in activated follicles, its mRNA is localized in primordial follicles closest to the medullar region and labeling is more intense in the transitional and primary follicles. Thus the labeling pattern will appears as a gradient of signal, undetectable in the cortex and more intense toward the medullar region.

FIG. 1 is the diagram showing a generalized overview of follicular development This diagram depicts the development of a dormant primordial follicle into a large mature follicle. Ultimately the mature follicle may be stimulated to ovulate and produce a fertilizable egg. This general process is the key for the production of eggs in many species.

FIG. 2 is a schematic diagram representing the many potential steps and control points for follicular development. The ovary is depicted as a reservoir of dormant follicles and through the process of follicular development these dormant follicles will develop and mature to subsequently produce hundreds to thousands of eggs. Depicted is follicular development as a pipeline and the control of this process consisting of many valves or potential regulatory steps. In the later stages of follicular development it is known that FSH is important for growth and development of mature antral follicles. Ultimately, LH stimulates the ovulations of a mature follicle and the production of the egg. However, the factors regulating early steps of follicular development have been essentially unknown for many years. The present invention was developed as an understanding how some of these early regulatory points are controlled in ovarian follicular development.

FIG. 3 is a diagram showing the later stages of follicular development that occur in growing follicles when they respond to stimulation by FSH where they mature into antral follicles. These are readily observable by morphological changes in histological sections of ovaries. However, in the early stages of follicular development the morphological changes are not as obvious during the activation of dormant primordial follicles. Before questions about the regulation of the activation and development of these early stage follicles could be focused. Identity of genetic markers which could be detected and measure molecular changes in activated primordial follicles was necessary. These markers are genes that are turned on in the process of activation of dormant follicles that can be observed before any morphological changes take place. One family of genes that was known to be expressed in early stages of follicular development is the one for the zona pellucida. The zona pellucida is the glycoprotein matrix (ring around egg) that surrounds the mature oocyte. Note the lack of protein matrices which surrounds the egg in the dormant follicle and the outer line in the growing follicle that indicates the presence of zona pellucida.

Table 1 lists all the genes for zona pellucida proteins that are present in four species. the rabbit, pig, mouse, and human. These have all been cloned and published. The zona pellucida gene that was chosen to investigate was the R55 gene in rabbit. The homologue this gene in the pig is ZP3α and there are similar genes present in the mouse and a human known as ZP1. First studies were designed and carried out in the rabbit so those studies are described first; R55was studied to determine if this gene fits criteria as a early to marker or indicator for activation of dormant primordial follicles.

TABLE 1

ZP Nomenclature

| | |
|---|---|
| Rabbit: | R45, R55, and R75 |
| Pig: | ZP3β, ZP3α, ZP2 and ZP1 |
| Mouse: | ZP3, ZP2, and ZP1 |
| Human: | ZP3, ZP2 and ZP1 |

Figure 4:
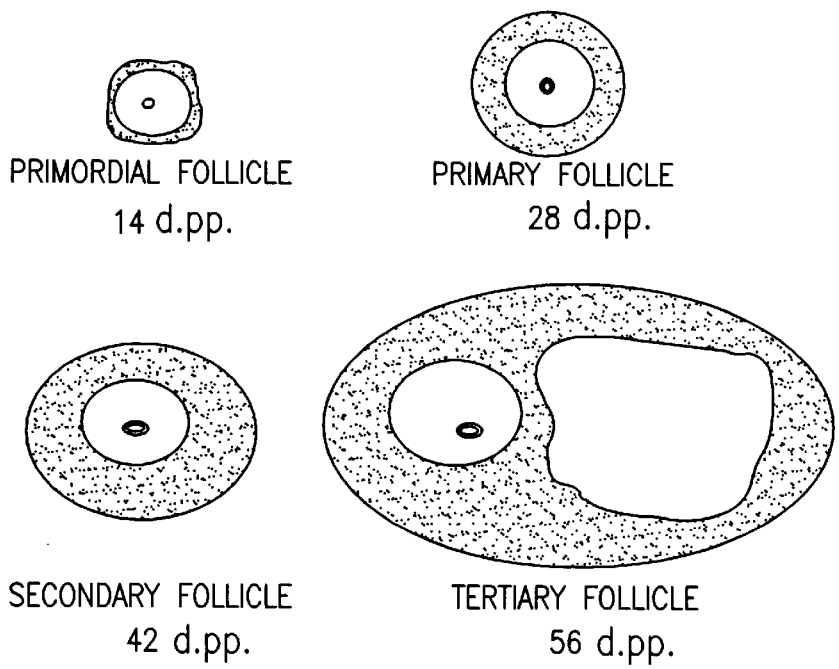
FIG. 4 is a diagram that shows the different stages of follicular development that are present in prepubertal rabbits.

FIG. 4 shows the different stages of follicular development that are present in prepubertal rabbits. This is one of the reasons this species was selected for study. In prepubertal rabbits, ovarian development occurs after birth (humans are more like pigs in their temporal developmental profile). Because of this fact, ovaries from different ages of prepubertal rabbits were taken and with more mature follicles at each age. As shown in the fourteen day post-partum rabbit (which means fourteen days after birth) the ovary is essentially a bag of primordial follicles. At 28 days post-partum, a group of follicles have begun to develop and resulting in a population of primary follicles, which are morphologically different from the primordial follicles in that they contain a single layer of cuboidal granulosa cells surrounding the follicle. 42 days post-partum secondary follicles are present indicating yet another step of maturation in the early development of follicles. And by 56 days postpartum, tertiary follicles begin to appear which represent early stages of antral development in the ovarian follicles. The expression of the R55gene is linked to the activation in early development of ovarian follicles, i.e. its pattern of expression following this initial wave of follicular genesis.

Figure 5:
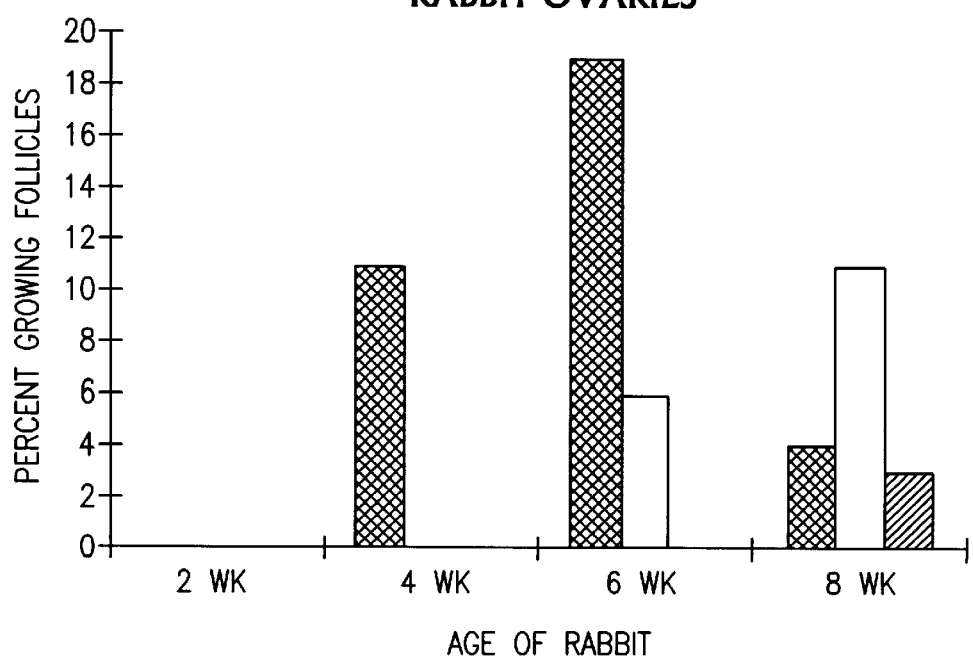
FIG. 5 is a graph demonstrating the first wave of follicular development in prepubertal rabbits.

FIG. 5 graphically demonstrates the first wave of follicular development in prepubertal rabbits. A peak in the percentage of follicles initiating development (primary follicles) is seen around 6 weeks of age. These data are based on morphological characterization of histological sections and are presented in Table 2.

TABLE 2

Percentage of follicles present in rabbit ovaries of different ages.

| | 2 wk | 4 wk | 6 wk | 8 wk |
|---|---|---|---|---|
| Primary | 0 | 11 | 19 | 4 |
| Secondary | 0 | 0 | 6 | 11 |
| Tertiary | 0 | 0 | 0 | 3 |
| Primordial | 100 | 89 | 75 | 80 |

Figure 6:
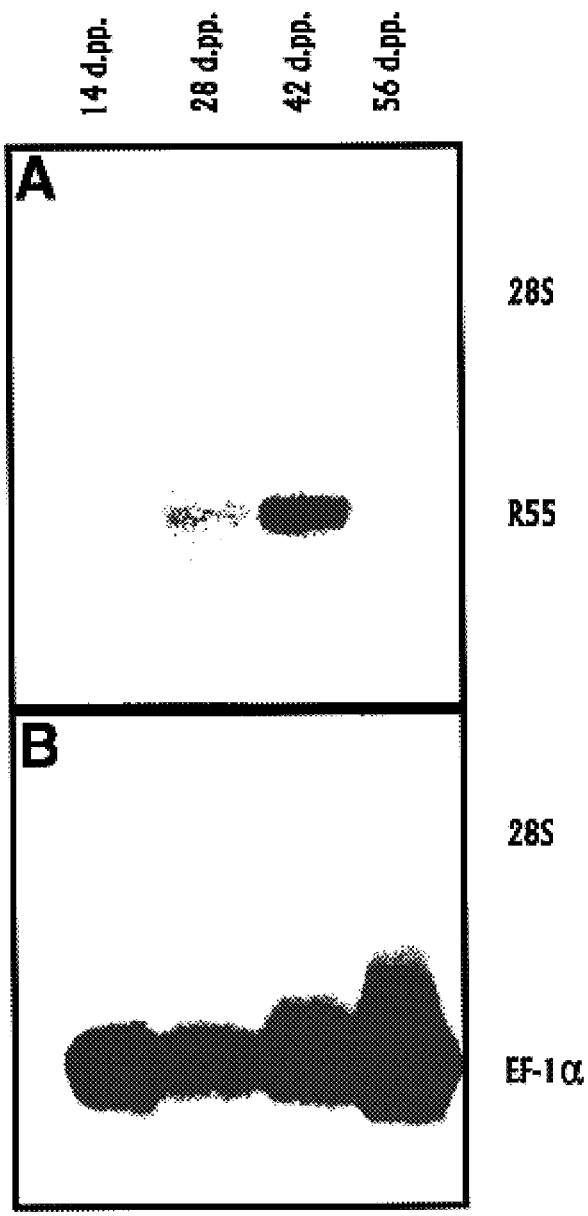
FIG. 6 is a photograph representation showing the Northern blot analysis of R55 in the immature rabbit ovaries.

FIG. 6 shows the northern blot analysis of R55 in immature rabbit ovaries. In this study, total RNA was isolated from different age rabbit ovaries, separated on agarose gels and transferred to biotrans nylon membranes. The membrane was then probed with a cDNA probe for R55 labeled with $P^{35}$ and developed by autoradiography. As shown in panel A, R55 is undetectable at 14 days postpartum. A more intense band at 28 days postpartum and a very dark band at 42 days postpartum is presented. The R55 band is less intense at 56 days postpartum. This blot was then stripped and reprobed with a constitutive gene EF1α to show equal loading and transfer of the RNA. This experiment was repeated with 3 different groups of RNA. The intensity of the bands were determined by optical density and the data shown graphically.

Figure 7:
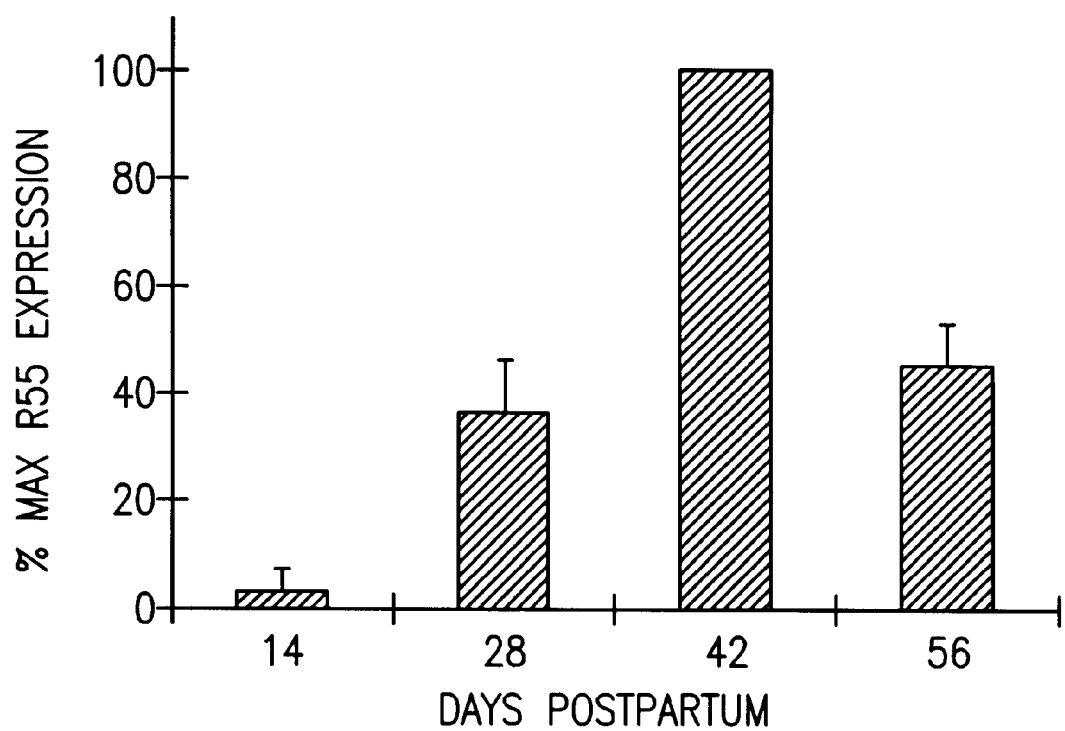
FIG. 7 is a graph showing R55 expression in developing rabbit ovaries.

FIG. 7 is a graphic showing R55 expression in developing rabbit ovaries. The pattern of R55 expression correlates with the pattern from the first wave of folliculogenesis in the prepubertal rabbits as shown in FIG. 5. This graph was obtained by determining the ratio of R55 to EF 1α from each sample and then this number was graphed as a relative percentage of the maximum R55 expression found. Data supporting the graph of FIG. 7 are presented in Table 3.

TABLE 3

R55 expression in rabbit ovaries from different ages.
Percent of maximum expression of R55 mRNA was determined on
Northern blots. Maximum expression occurs at 42 days
postpartum d.pp.)

| d.pp. | 14 | 28 | 42 | 56 |
|---|---|---|---|---|
| % Max R55 | 3.1 | 36 | 100 | 45 |
| SEM | 1.8 | 9.8 | 0 | 7.3 |

Figure 8:
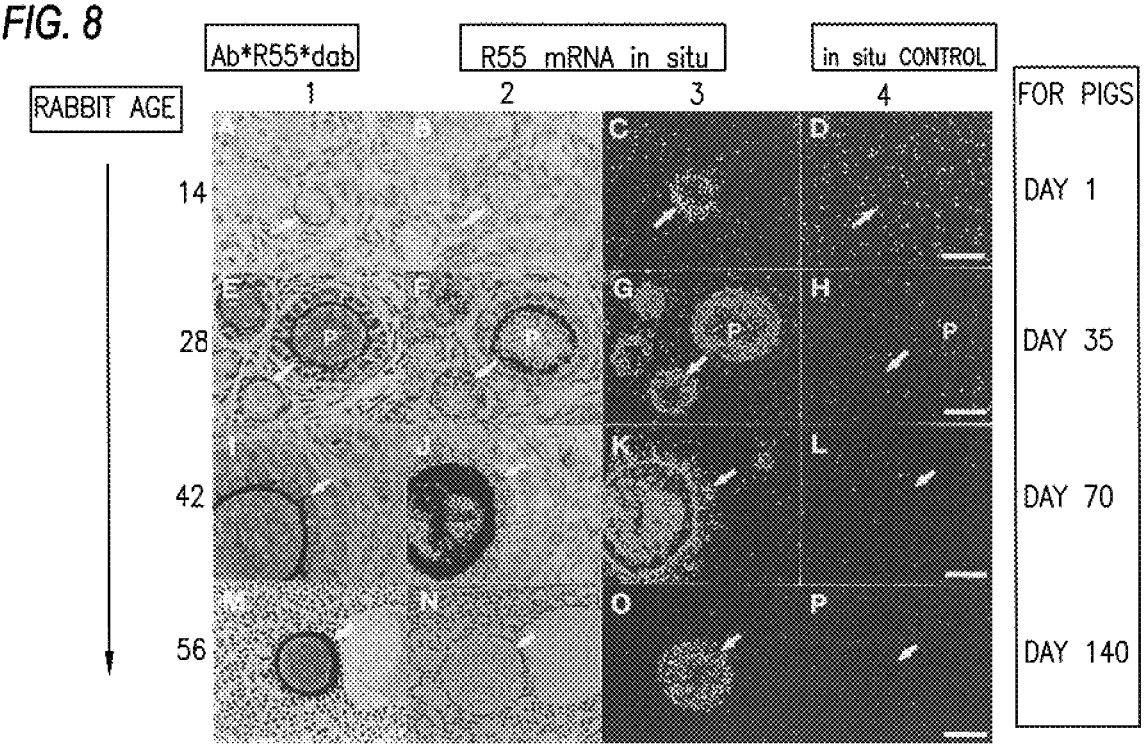
FIG. 8 is a composite representation showing the localization of R55 protein and messenger RNA in developing ovaries of prepubertal rabbits.

FIG. 8 is a composite showing the localization of R55 protein and messenger RNA in developing ovaries of prepubertal rabbits. Column 1 is the localization of R55 protein as determined by antibody staining with DAB conjugate. Columns 2 & 3 are in situ hybridizations for R55 messenger RNA. Column 4 is the in situ control using the sense strand as the riboprobe. The anti-sense strand was used in columns 2 and 3 all of which were labeled with $S^{35}$. In the first row a single primordial follicle labeled for R55 protein and mRNA is shown. Based on hypothesis it is shown that this primordial follicle even though it has not undergone any morphological changes has begun to develop since it is it expressing the R55 gene.

In the second row it is shown that the primary follicles that appear by 28 days postpartum are expressing significant amounts of R55 protein and mRNA. Also important in this section shown by the arrow is a follicle which we would term to be an intermediate follicle. It is somewhere in transition between the stages of primordial and primary and again as we would expect it is expressing a significant amount of R55. This is consistent with our prediction. In the third row is a section taken from a six week old rabbit (42 days postpartum). In this section we show a secondary follicle which contains abundant amounts of zona pellucida protein beginning to form in a matrix around the oocyte in the first panel.

In the second and third panels it is shown that the oocyte contains a large quantity of mRNA for R55. Not shown in this section are the many primary follicles which are present in 42 days postpartum which are also expressing abundant levels of R55. At 56 days postpartum in the fourth row a developing follicle is shown and by this stage a thick well developed matrix has formed around the oocyte which is a dark layer around the oocyte. In the second and third panels it is shown that the amount of mRNA for R55 is dramatically decreased from what is seen in secondary follicles.

Figure 9:
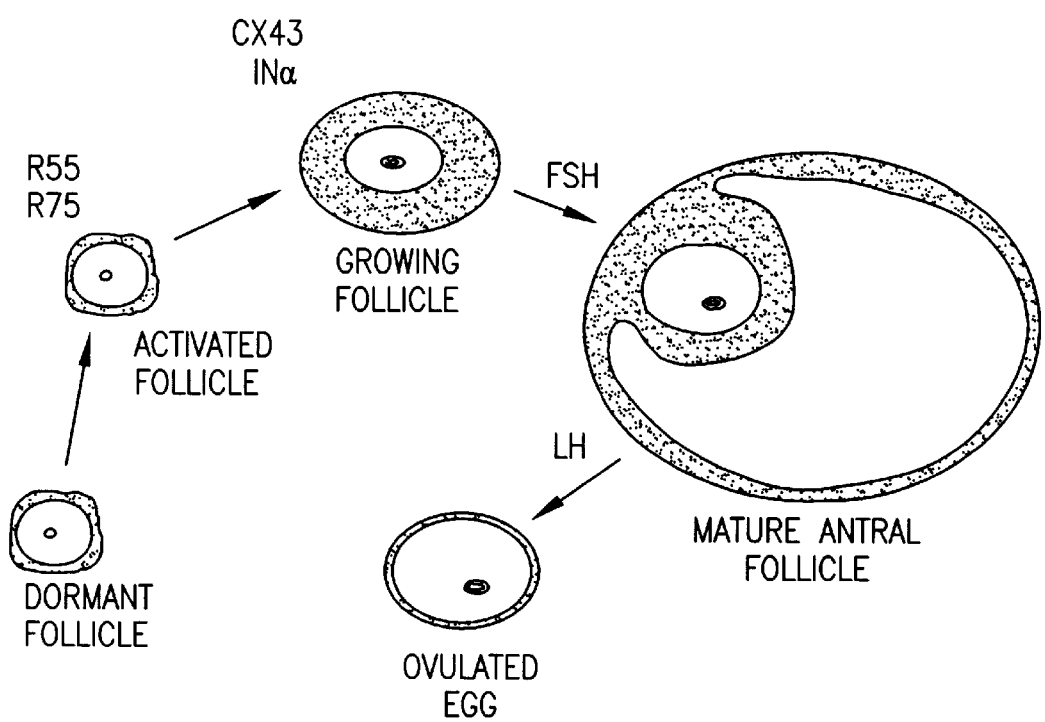
FIG. 9 is a diagram showing that a second ZP gene in the rabbit R75 is a valid marker for activation of primordial follicles and its pattern of expression which is similar to R55.

Returning to initial study steps of follicular development, a marker R55 is initially expressed in activated follicles in the rabbit ovary. FIG. 9 shows that it was determined that a second ZP gene in the rabbit R75 is a valid marker for activation for primordial follicles in its pattern of expression is similar to P55 so this gives two genes which can be measured in follicles to determine whether they are activated or not. Additionally, in rabbit two other genes were identified which are specific to granulosa cells and are expressed in these cells during the transition from primordial to primary follicles. (Cx43 (connexin 43) and Inhibin-alpha). Now with these markers in hand questions about potential regulatory factors that might stimulate or inhibit activation dormant primordial follicles were considered.

Figure 10:
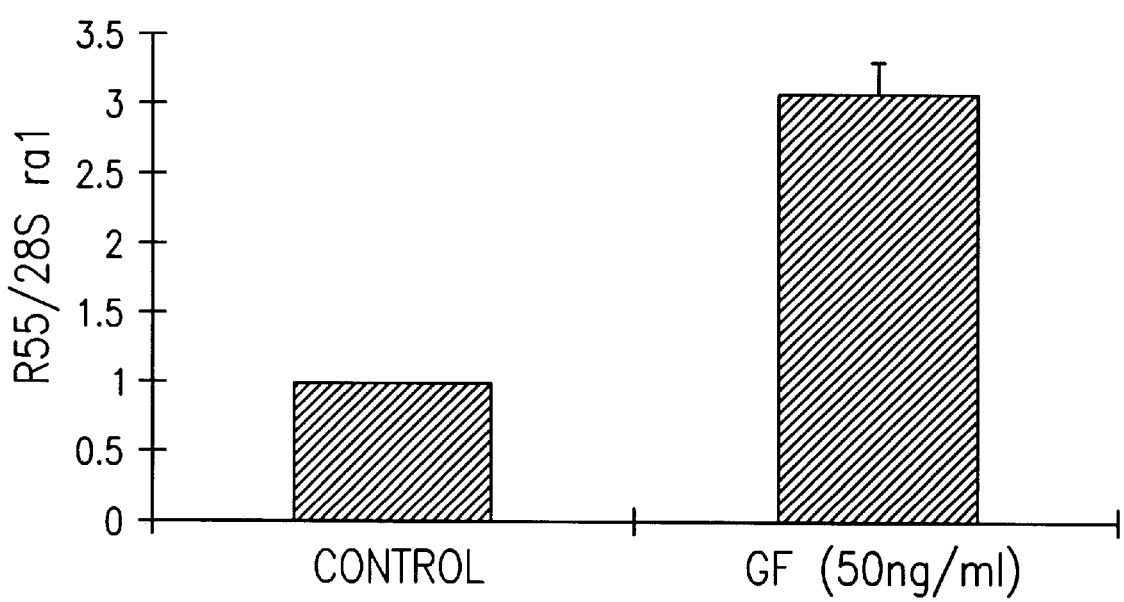
FIG. 10 is a graph showing the effects of growth factors (epidermal growth factor, EGF) on R55 expression in immature rabbit ovaries.

FIG. 10 shows the effects of growth factors EGF on R55 expression in immature rabbit ovaries. Ovaries were collected from 2 week old rabbits and the tissue mince into small pieces (~1 $mm^3$). These ovarian explants were then cultured for 6 days in the presence or absence of EGF (50 ng/ml). Total RNA was isolated and the relative amount of R55mRNA measured by Northern blot analysis. The result of 3 experiments were averaged and graphed. The level of P55 expression in the controls was defined as one. The level of expression of the epidermal growth factor treated samples was approximately 3 fold of that seen in the controls. This indicates that with treatment of epidermal growth factor there was a significant increase in the expression of R55 in these ovarian cultures. This effect is due to an increase in the number of follicles being activated. Data supporting the graph of FIG. 10 are presented in Table 4.

TABLE 4

Results of 3 experiments showing stimulation of R55 mRNA expression by EGF. Values are the ratio of R55 to 28S optical densities from Northern blots.

|  | Control | EGF (50 ng/ml) |
| --- | --- | --- |
| Exp. 1 | 1 | 2.87 |
| Exp. 2 | 1 | 3.09 |
| Exp. 3 | 1 | 3.28 |
| Average | 1 | 3.08 |
| Std dev. | 0 | 0.20518285 |
| SEM | 0 | 0.11846237 |

FIG. 11 is directed to ovarian development in prepubertal pigs to determine if the inventive method would be applicable in other species. FIG. 11 shows comparison of 10 week old pig ovaries to ovaries which are typical of a mature sow. In the rabbit, much (but not all) of the ovarian development occurs after birth. In the pig, ovarian development overlaps both the rabbit and human in developmental timetable. Development occurs over an extended period of time such that at 10 weeks the ovaries are very small and relatively immature. In pigs, antral follicles are normally not seen until 140 to 150 days (20 weeks) of age. This timetable may be accelerated by application of systemic EGF.

Figure 12:
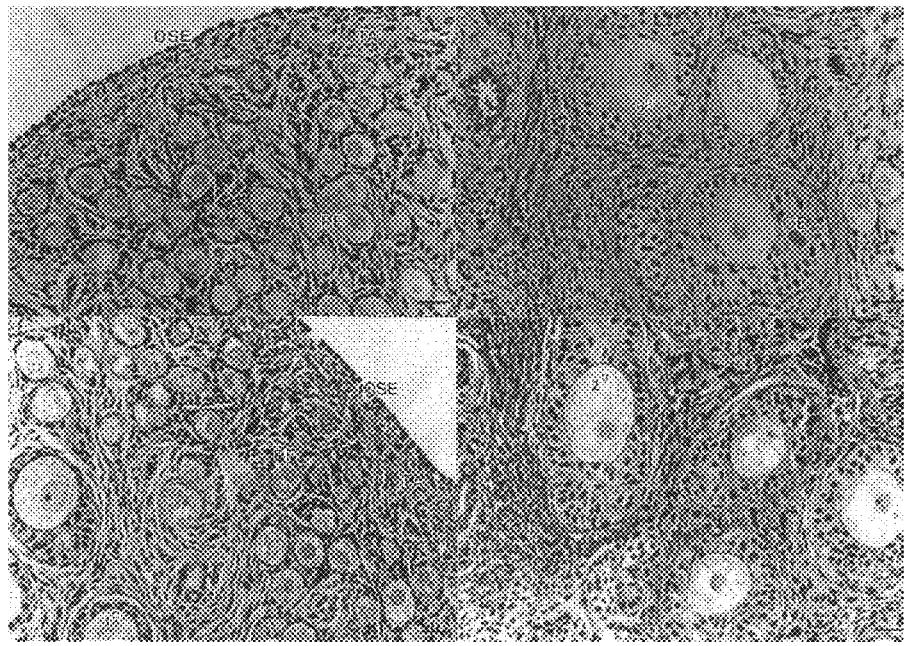
FIG. 12 presents the follicle populations present in the immature pig ovaries at day 70 postpartum or 10 weeks of age.

FIG. 12 shows the follicle populations present in the immature pig ovaries at day 70 postpartum or ten weeks of age. In the two panels on the left it is shown that a large population of primordial follicles are present in the cortex of ten week old pig ovaries. These represent the dormant or resting pool of primordial follicles which will ultimately give rise to all the eggs which the gilt will produce throughout her life. In the two panels to the right it is seen that in these same ovaries many secondary follicles are growing and developing. Based on morphology the 10 week pig ovary is very similar to the 42 day postpartum rabbit ovary.

Figure 13:
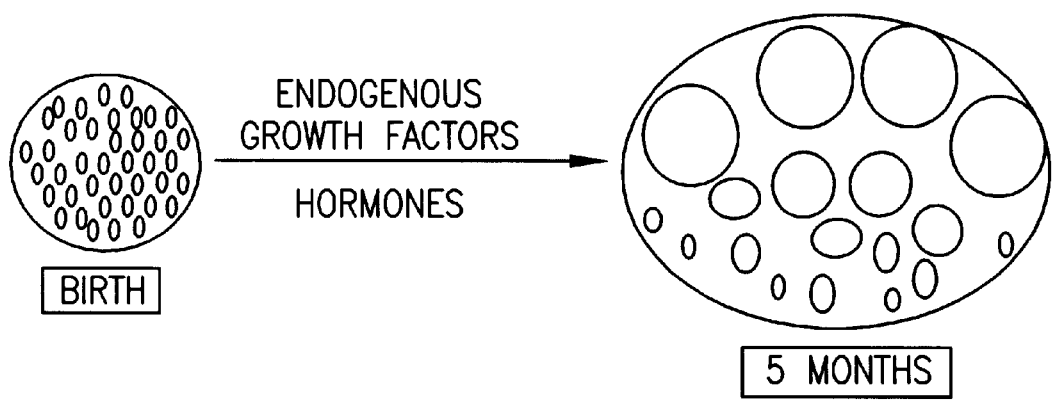
FIG. 13 is a schematic depicting the follicle development that occurs during ovarian maturation in the prepubertal pig.

FIG. 13 diagrammatically depicts the follicular development that occurs during ovarian maturation in the pig. At birth the ovary is primarily filled with dormant primordial follicles. Through the first 5 months of the gilts life the ovary matures and develops through the stimulation of endogenous growth factors and hormones such that at 5 months of age there's a large population of antral follicles. These antral follicles are ready to be ovulated and will produce the eggs that are ovulated during the first heat.

Figure 14:
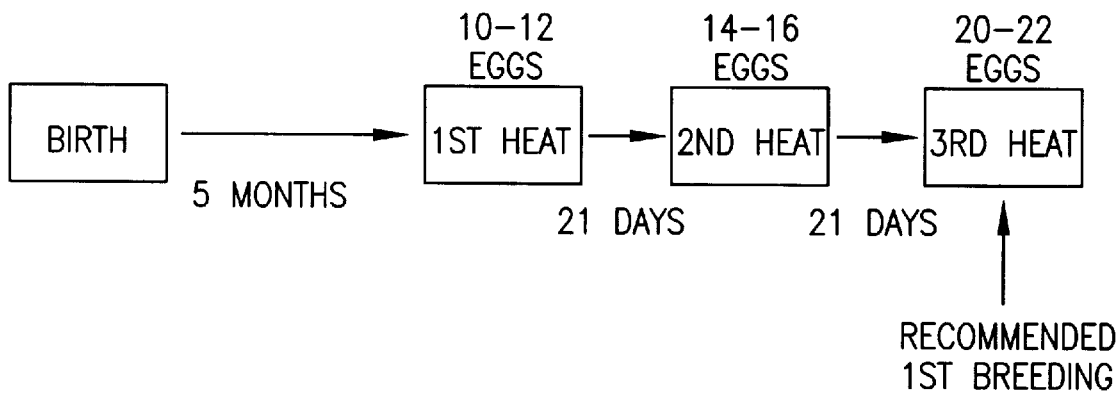
FIG. 14 presents a schematic that shows the reproductive maturation timeline as relative to the situation found with commercial gilts.

FIG. 14 shows the reproductive maturation timeline as relative to the situation found with commercial gilts. As depicted from birth through the first 5 months the ovary develops and matures. At about this time the gilt will undergo her first heat. At this first heat there's typically 10 to 12 eggs ovulated. After another 21 days the gilt will enter her second heat at which there will be slightly more eggs ovulated, 14 to 16. After another 21 days the gilt will enter her third heat at which there will be 20 to 22 eggs ovulated and at this point it is the recommended time for first breeding of a gilt. In this diagram we can emphasize two obvious goals for the inventive method to accelerate ovarian maturation. One would be to increase the number of eggs ovulated in the first or second heat, such that commercial pork producers could then breed at these earlier times. Thus, saving time and feed costs while getting the most (larger litters) out of their immature gilts. Secondly, the inventive process could potentially shorten the period of time, the 5 month period, the gilt requires to reach the first heat. Both of these results combined would result in significant savings for the pork producer and the end result would be more pigs per litter earlier.

Figure 15:
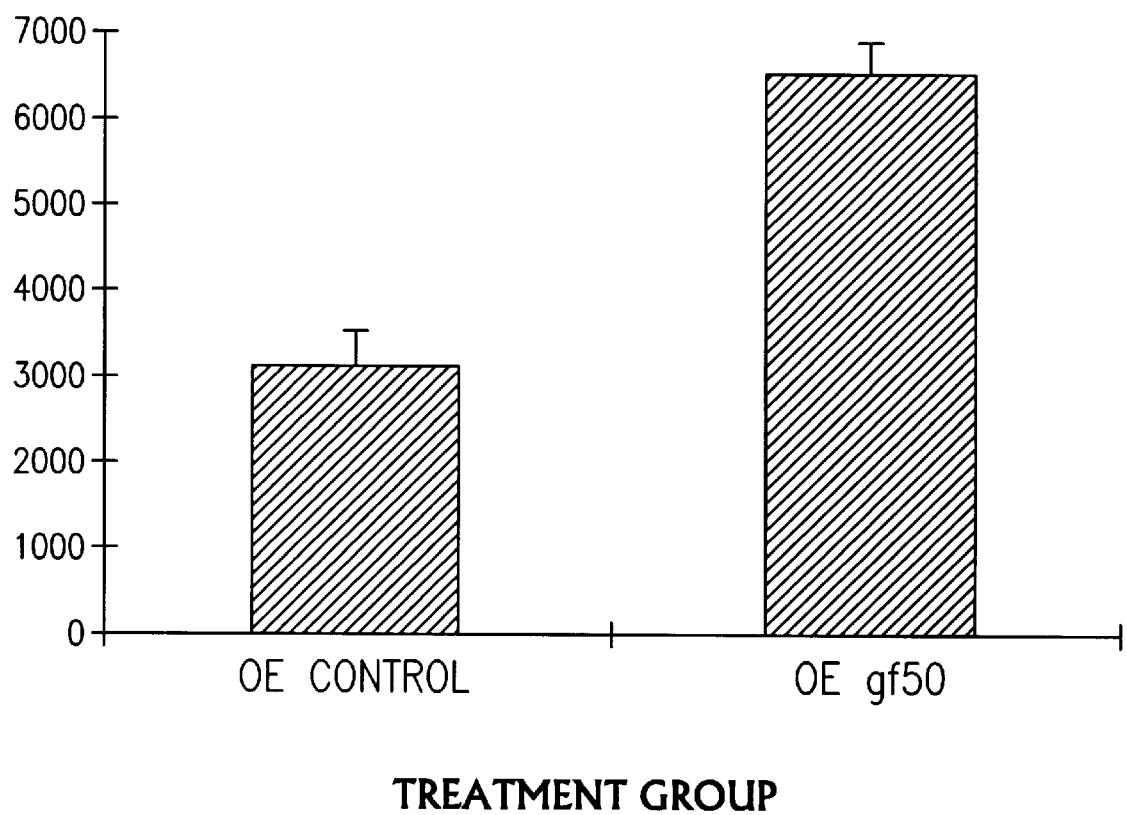
FIG. 15 is a graph showing the inventive results established in the rabbit was applicable to the pig.

FIG. 15 shows the inventive results established in the rabbit was applicable to the pig and it was determined to look at the effect of growth factors, specifically EGF, on ZP expression in immature pig ovaries. For this first experiment ovaries were collected form pigs at three to five weeks of age at which the pig ovaries are very immature. The ovaries were then minced into small pieces and grown in ovarian explant cultures with or without EGF (similar to what we have done with the rabbit ovaries). After 6 days of culture the tissue was collected and in this case proteins from these samples were isolated and solubilized. The amount of total zona pellucida protein in these samples was determined using an antibody we developed in guinea pigs against total zona pellucida proteins. The amount of porcine zona pellucida proteins in these samples were determined by dot blot analysis and quantified by optical density. The relative amount of zona pellucida protein is graphed for each sample (control and EGF treated 50 ng/ml). This was done for 3 replicates. These studies resulted in approximately a two fold increase in the amount of zona pellucida protein in the EGF treated ovarian explants. These results were consistent with the stimulation of P55 expression which shown in the rabbit ovarian explants. Data supporting the graph of FIG. 15 is presented in Table 5.

TABLE 5

Stimulation of pig ZP proteins with EGF.
Optical density of ZP proteins from ovarian explant cultures as measure by Protein dot blot analysis.

| Group ZP | OE EGF 50 | OE control |
| --- | --- | --- |
|  | 6355 | 2493 |
|  | 6086 | 3763 |
|  | 7193 | 3160 |
| Avg. ZP | 6544.66667 | 3138.66667 |
| Std. Dev. | 577.358063 | 635.26871 |
| SEM | 333.337833 | 366.77256 |

Figure 16:
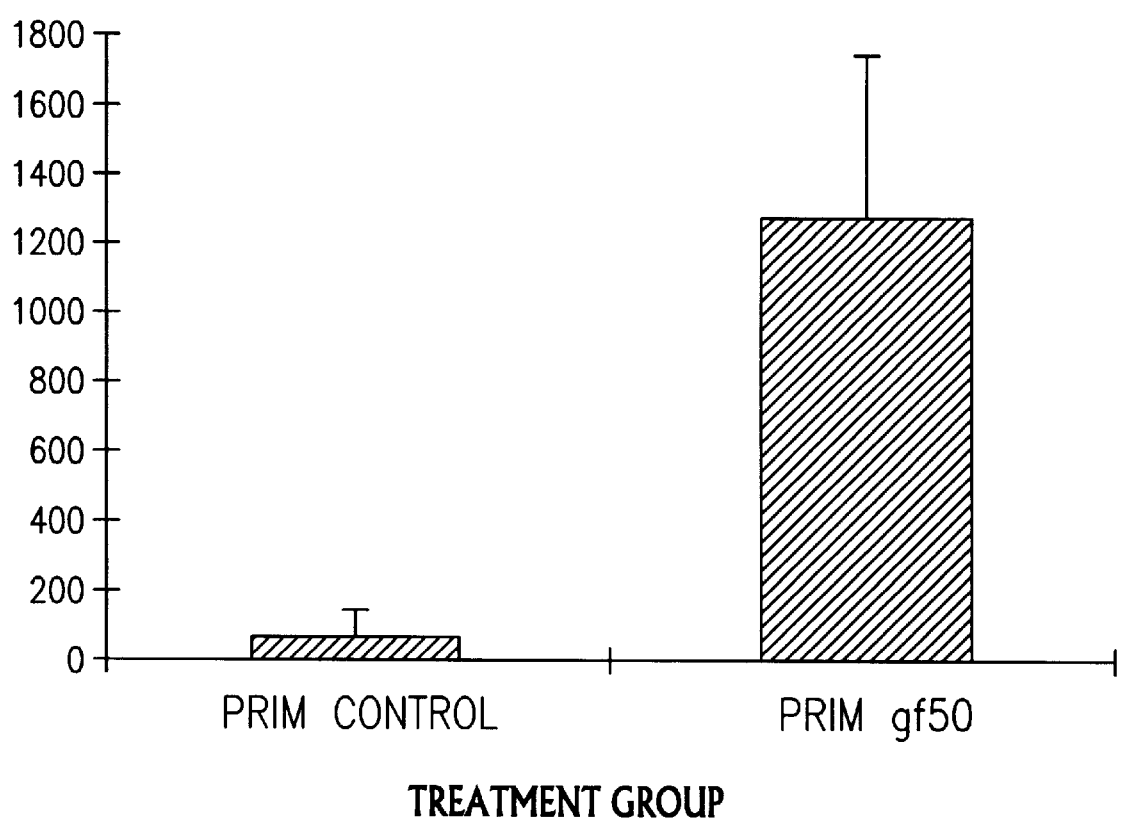
FIG. 16 is a graph showing the effect of EGF on ZP expression in isolated primordial porcine or pig follicles.

FIG. 16 graphically presents the results of studying the effect of EGP on ZP expression in isolated primordial follicles. As in the previous experiment, ovaries were collected from immature pigs at 3 to 5 weeks of age. In this case the ovaries were minced and the follicles enzymatically separated from the connective tissues and isolated. The population of small primordial follicles were collected and grown in cell culture well inserts. These were cultured for six days in medium alone as control or in medium supplemented with 50 nanograms per ml of EGF. After 6 days of culture the follicles were collected and proteins isolated and solubilized. The amount of total zona pellucida protein in these samples was determined using an antibody developed in guinea pigs against total zona pellucida proteins. The amount of porcine zona pellucida proteins in these samples were determined by dot blot analysis and quantified by optical density. The relative amount of zona pellucida protein is graphed in FIG. 16 for each sample (control and EGF treated 50 ng/ml). This was done for 3 replicates. As predicted from the hypothesis there was a significant increase in the expression of zona pellucida proteins in the primordial follicles treated with EGF. This is consistent with the hypothesis that EGF can stimulate activation of dormant primordial follicles as indicated by the expression of zona pellucida genes. Data supporting FIG. 16 is presented in Table 6.

TABLE 6

Stimulation of pig ZP proteins in isolated primordial follicles with EGF. Optical density of ZP proteins from cultured primordial follicles as measured by Protein dot blot analysis.

| Group ZP | Primordial & EGF 50 ng/ml | Primordial, control |
|---|---|---|
|  | 1815 | 230 |
|  | 371 | 9.85 |
|  | 1697 | 0 |
| Avg. ZP | 1294.33333 | 79.95 |
| Std. dev | 801.8038 | 130.040407 |
| SEM | 462.92164 | 75.0788641 |

Figure 17:
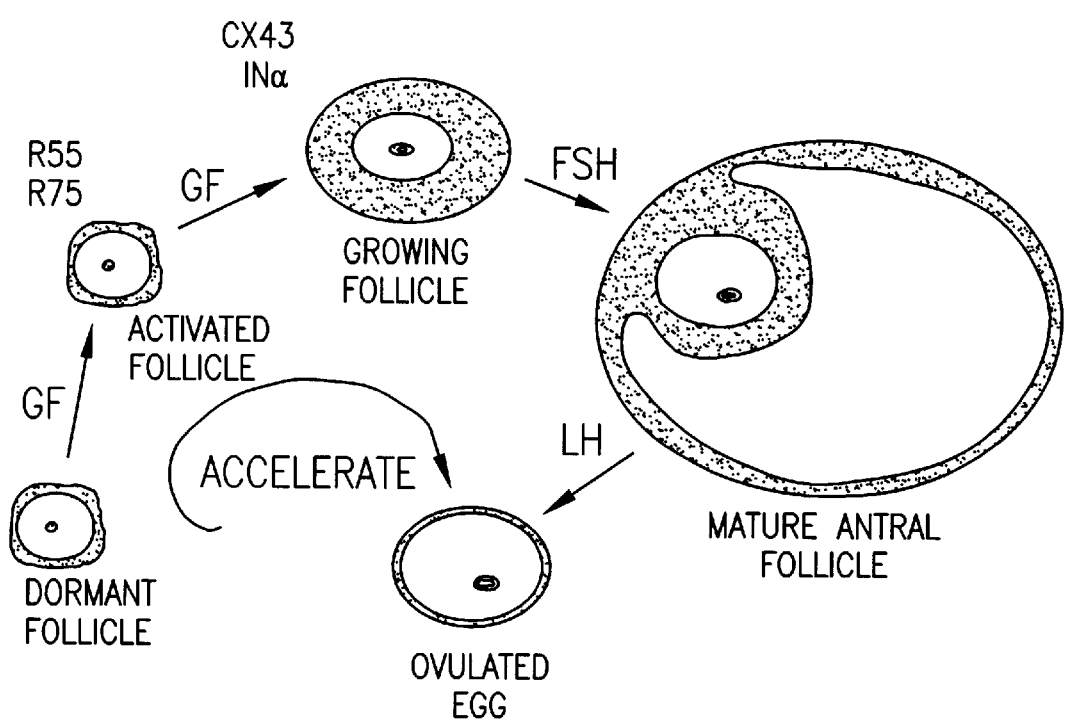
FIG. 17 is a diagram summarizing overall basic working model for acceleration of follicular development in accordance with the invention.

FIG. 17 summarizes overall basic working model for acceleration of follicular development. Growth factors, specifically EGF, applied in early follicular development results in the acceleration of this process. In other words EGF will stimulate the activation of dormant follicles and accelerate their development in the early stages of growth. An increased number in activated follicles will ultimately result in an increased number of follicles present and potentially available for maturation under the stimulation of FSH into large mature antral follicles, which at the LH surge would be ovulated. The end result would be more ovulated eggs and a shorter period of time for follicular development. This process can be applied to prepubertal development in the gilt (young sow) or other vertebrates to initiate or accelerate ovarian maturation and result in two positive effects. One being the increase in the number of eggs in early heats for the gilts and other species and two, possibly a shorter period of time to reach the first heat in these animals such that pork producers may be able to breed earlier and get more pigs per litter earlier in these animals.

FIG. 18 is the DNA and amino acid sequences of encoding rec-pEGF protein. Rec-pEGF was expressed in the QiaExpress plasmid vector pQE30. The DNA sequence encoding pEGF begins at the adenine residue 36, with the AAT codon, encoding $N^{13}$, and ends at the cytosine residue 193 and the codon encoding $Tyr^{65}$. The DNA and amino acid sequence contains the 6X histidine tag at the amino-terminal end, and 19 amino acids from the bacterial plasmid vector at the COOH-terminal end. The 53 amino acids of the rec-pEGF is 100% identical to the published sequence for rec-pEGF published by Pascall, J. C., et al., *J. Mol. Endocrinol.* (1991) 6:63–70, which is hereby incorporated by reference as teaching a method for obtaining rec-pEGF using yeast and bacteriophage vectors.

FIG. 19 is the results of gel electrophoresis on 15% polyacrylamide SDS gels, of expressed rec-pEGF protein purified on a Ni-Agarose column, showing a representative sample of some of the gels showing two purified samples of rec-pEGF. Lane 1 is a gel showing flow through of unbound bacterial proteins from a first sample run. Lane 2 is a gel showing a buffer wash of the column. Lane 3 shows a relatively pure sample of rec-pEGF at a relative molecular weight of about 10 kDa, corresponding to the predicted molecular weight from the amino acid sequence of FIG. 18. Lane 4 is a flow through sample of unbound bacterial proteins from a second sample run. Lane 5 is a gel showing a buffer wash of the column. Lane 6 shows a relatively pure sample of rec-pEGF at a relative molecular weight of about 10 kDa, corresponding to the predicted molecular weight from the amino acid sequence of FIG. 18. Finally lane 8 is the molecular weight markers.

Figure 20:
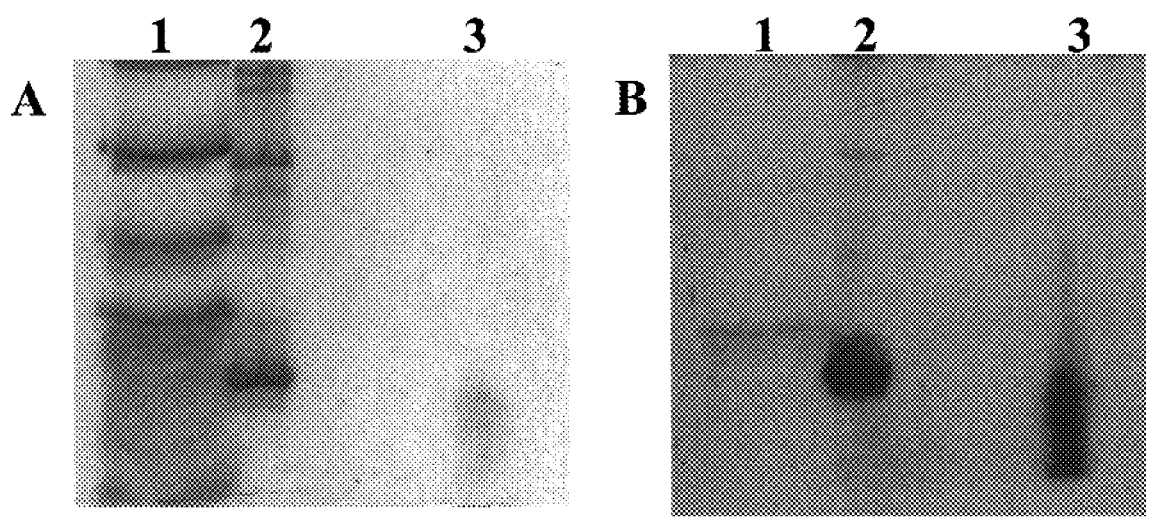
FIG. 20 are Western blots of rec-pEGF, in which panel A is a coommassie stained 1D-PAGE gel and panel B is mouse EGF antibodies detected with chemiluminescence.

FIG. 20 is a Western blot assay performed to verify the identify of the rec-pEGF obtained by gel electrophoresis. The protein was transferred to an Immobilon membrane and analyzed with commercially available antibodies to mouse EGF. Panel A illustrates a coomassie stained gel of rec-pEGF and mouse EGF on a 1D-PAGE gel, and panel B illustrates the rec-pEGF and mouse EGF proteins which are recognized by rabbit anti-mouse EGF (Upstate Biotechnology, Incorporated) and detected which chemiluminescence. In both panels A and B, lane 1 is a molecular weight marker, lane 2 is 5.5 μg of rec-pEGF, and lane 3 is 0.25 μg mouse EGF.

Figure 21:
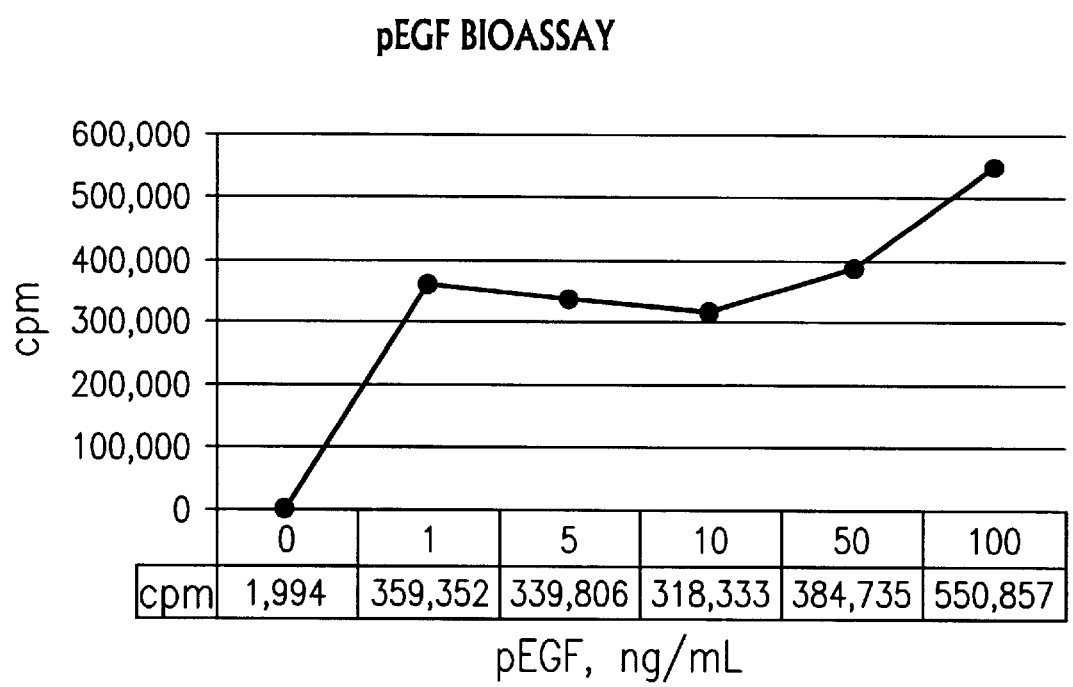
FIG. 21 is a graph of a fibroblast proliferation assay using tritiated tymidine uptake to determine the effect of increasing rec-pEGF concentrations on DNA synthesis.

In FIG. 21, the bioactivity of EGF was tested in a 3T3 fibroblast proliferation assay. EGF was added to quiescent Swiss 3T3 fibroblast cells and stimulation of fibroblast proliferation was measured by $[H^3]$-thymidine incorporation as an indicator of DNA synthesis. Stimulation of fibroblast proliferation by rec-pEGF was comparable to that of purified mouse EGF.

FIG. 22 is a graph comparing the average size of the ten largest follicles observed in histological sections of ovarian obtained from necropsy samples of the pigs in Group 1, above, comparing follicle size to that of the control group and the group administered nothing. Follicular diameter was measured using an ocularmicrometer and only sections through the center of a follicle, having the germinal vesicle present, were used for the evaluation. It will be appreciated that the follicle size in the pigs given rec-pEGF were over 100% greater in diameter than that of the control group and over 70% greater than that of the group given nothing. Similarly, Table 7, below, offers a comparison of the organ weights of control and EGF-treated pigs in Group 2, and demonstrate the lack of effect of rec-pEGF on organ weights, body weights and general pathology.

TABLE 7

| Measure | Control N = 3 | EGF N = 3 | Treatment P Value |
|---|---|---|---|
| Day 14 Weight (kg) | 4.9 ± 0.24 | 4.6 ± 0.24 | 0.46 |
| Day 70 Weight (kg) | 24.5 ± 3.40 | 22.7 ± 3.40 | 0.72 |
| Avg. Daily Gain (kg/d) | 0.35 ± 0.06 | 0.32 ± 0.06 | 0.76 |
| Heart (gm) | 124.4 ± 11.3 | 114.4 ± 11.3 | 0.56 |
| Heart (% Body Weight) | 0.52 ± 0.03 | 0.51 ± 0.03 | 0.91 |
| Spleen (gm) | 129.6 ± 38.1 | 112.0 ± 38.1 | 0.76 |
| Spleen (% Body Weight) | 0.53 ± 0.13 | 0.48 ± 0.13 | 0.82 |
| Liver (gm) | 703.9 ± 71.3 | 622.6 ± 71.3 | 0.50 |
| Liver (% Body Weight) | 2.91 ± 0.16 | 2.77 ± 0.16 | 0.57 |
| Uterus (gm) | 8.06 ± 0.82 | 8.15 ± 0.82 | 0.94 |
| Uterus (% Body Weight) | 0.034 ± 0.006 | 0.037 ± 0.006 | 0.77 |
| Ovary (gm) | 0.18 ± 0.085 | 0.36 ± 0.86 | 0.21 |
| Ovary (% Body Weight) | 0.0008 ± 0.0003 | 0.0018 ± 0.0003 | 0.23 |
| Kidney (gm) | 151.8 ± 18.1 | 139.8 ± 18.12 | 0.81 |
| Kidney (% Body Weight) | 0.62 ± 0.07 | 0.64 ± 0.74 | 0.86 |

Finally, FIG. 23 is a graph which confirms that in vivo administration of rec-pEGF to the Group 1 pigs, above, starting at 30 d.pp. and administered for fourteen consecutive days at a 540 μg/day dose by placement of subcutaneous osmotic pumps in each pig. Ovaries from a sub-set of Group 1 pigs were examined at 70 d.pp. when the first cohort of growing follicles is normally expected to be present. The data demonstrates clearly that the number of ovarian follicles were significantly increased by application of rec-pEGF over the control group and the group administered nothing. Data was obtained by counting the number of hematoxylin/eosin stained follicles in a counting frame (960×1400 µm), and only sections through the center of a follicle with the germinal vesicle present were used for the evaluation. Growing follicles were identified based upon the presence of at least one cuboidal layer of granulosa cells surrounding the oocyte.

The data clearly supports the proposition that administration of exogenous EGF accelerates ovarian development, increases ovulation rate at an age earlier than in untreated mammals, and increases the rate of ovarian maturation in prepubertal vertebrates. Additionally RNA samples were transferred to nylon membranes and will be evaluated for relative amounts of Z3β mRNA and will conform an increased level of follicular analysis by Northern blot analysis.

Although the invention has been described with respect to specific embodiments, it should be appreciated that other embodiments utilizing the concept of the present invention are possible without departing from the scope of the invention. The invention, for example, is not intended to be limited to the specific mammals discussed and exemplified and disclosed in these embodiments; rather the invention is defined by the claims in equivalence thereof.

What is claimed is:

1. An in vivo method for increasing litter size in a pig, comprising parenterally administering epidermal growth factor to said pig in an amount effective for increasing the litter size born to said pig.

2. The method of claim 1 wherein the epidermal growth factor is to said pig when the pig is about 1 to about 70 days old.

3. The method of claim 1 wherein the epidermal growth factor is administered to said pig when the pig is about 1 to about 35 days old.

4. The method of claim 1 wherein the epidermal growth factor is administered to said pig in an amount of at least about 540 µg per day.

5. The method of claim 1 wherein the epidermal growth factor is administered to said pig in all amount up to about 540 µg per day.

6. The method of claim 1 wherein the epidermal growth factor is administered to said pig in an amount of about 540 to about 600 µg per day.

7. The method of claim 1 wherein the epidermal growth factor is administered to said pig in a treatment amount of about 7.5 mg.

8. The method of claim 1 wherein said epidermal growth factor is administered intramuscularly.

9. The method of claim 1 wherein said epidermal growth factor is administered via injection.

10. The method of claim 1 wherein said epidermal growth factor is administered via a subcutaneous osmotic pump.

11. An in vivo method for activating primordial ovarian follicles in a pig, comprising administering epidermal growth factor parenterally to said pig in an amount effective for activating said primordial ovarian follicles.

12. The method of claim 11 wherein the epidermal growth factor is administered to said pig when said animal is about 1 to about 70 days old.

13. The method of claim 11 wherein the epidermal growth factor is administered to said pig when said pig is about 1 to 35 days old.

14. The method of claim 11 wherein the epidermal growth factor is administered to said pig when said pig is about 35 to 70 days old.

15. The method of claim 11 wherein the epidermal growth factor is administered to said pig in an amount of at least about 540 µg per day.

16. The method of claim 11 wherein the epidermal growth factor is administered to said pig in an amount up to about 540 µg per day.

17. The method of claim 11 wherein the epidermal growth factor is administered to said pig in an amount of at least about 600 µg per day.

18. The method of claim 11 wherein the epidermal growth factor is administered to said pig in a treatment amount of at least about 8.4 mg.

19. The method of claim 11 wherein said epidermal growth factor is administered intramuscularly.

20. The method of claim 11 wherein said epidermal growth factor is administered via a route selected from the group consisting of injection and use of a subcutaneous osmotic pump.

21. A method for increasing the size of a pig ovary, comprising administering epidermal growth factor to said pig wherein said epidermal growth factor is administered intramuscularly in an amount effective for increasing the size of said ovary.

22. The method of claim 21 wherein the size of the ovary is increased by at least about 70%.

23. The method of claim 21 wherein the size of the ovary is increased by at least about 100%.

24. The method of claim 21 wherein the epidermal growth factor is administered to said pig when said animal is prepubertal.

25. The method of claim 21 wherein the epidermal growth factor is administered to said pig when said pig is from about 1 to about 70 days old.

26. The method of claim 21 wherein the epidermal growth factor administered to the pig in an amount of at least about 540 µg per day.

27. The method of claim 21 wherein the epidermal growth factor administered to the pig in an amount of up to about 540 µg per day.

28. The method of claim 21 wherein the epidermal growth factor administered to the pig in a treatment amount of at least about 7.5 mg.

29. The method of claim 21 wherein said epidermal growth factor is administered to said animal via injection.

30. The method of claim 21 wherein said epidermal growth factor is administered to said animal via a subcutaneous osmotic pump.

31. An in vivo method for increasing pig litter size, comprising administering at least about 540 µg of epidermal growth factor parenterally to a prepubertal pig; allowing said pig to attain puberty; and breeding said pig.

32. An in vivo method for increasing pig litter size, comprising administering up to about 540 µg of epidermal growth factor parenterally to a prepubertal pig; allowing said pig to attain puberty; and breeding said pig.

33. An in vivo method for increasing pig litter size, comprising administering a treatment amount of at least about 7.5 mg of epidermal growth factor parenterally to a prepubertal pig; allowing said pig to attain puberty; and breeding said pig.

34. The method of claim 31 wherein said epidermal growth factor is administered to said pig when the animal is from about 1 to about 70 days old.

35. The method of claim 31 wherein said epidermal growth factor is administered intramuscularly to said pig.

* * * * *